US007422896B1

(12) United States Patent
Wang

(10) Patent No.: US 7,422,896 B1
(45) Date of Patent: *Sep. 9, 2008

(54) COMPOSITIONS FOR DNA MEDIATED GENE SILENCING

(75) Inventor: Jiwu Wang, San Diego, CA (US)

(73) Assignee: Allele Biotechnology & Pharmaceuticals, Inc., San Diego, CA (US)

( * ) Notice: Subject to any disclaimer, the term of this patent is extended or adjusted under 35 U.S.C. 154(b) by 546 days.

This patent is subject to a terminal disclaimer.

(21) Appl. No.: 10/217,564

(22) Filed: Aug. 12, 2002

Related U.S. Application Data

(63) Continuation-in-part of application No. 10/202,479, filed on Jul. 23, 2002, now Pat. No. 7,294,504.

(60) Provisional application No. 60/343,697, filed on Dec. 27, 2001.

(51) Int. Cl.
*C12N 15/00* (2006.01)
*C12N 5/00* (2006.01)
*C12Q 1/68* (2006.01)
*A61K 31/70* (2006.01)
*C07H 21/04* (2006.01)

(52) U.S. Cl. .................. 435/320.1; 435/6; 435/325; 435/375; 536/24.5; 514/44

(58) Field of Classification Search ............... 536/24.5, 536/23.1; 514/44; 435/6, 325
See application file for complete search history.

(56) References Cited

U.S. PATENT DOCUMENTS

| 5,624,803 | A | * | 4/1997 | Noonberg et al. ............. 435/6 |
| 6,423,885 | B1 | | 7/2002 | Waterhouse et al. |
| 6,506,559 | B1 | * | 1/2003 | Fire et al. ..................... 435/6 |
| 2002/0086356 | A1 | | 7/2002 | Tuschl et al. |
| 2003/0027168 | A1 | | 2/2003 | Gan et al. |

FOREIGN PATENT DOCUMENTS

| WO | WO96/26963 | 9/1996 |
| WO | WO99/32619 | 7/1999 |
| WO | WO 99/53050 | 10/1999 |
| WO | WO 01/12824 A1 | 2/2001 |
| WO | WO01/29058 | 4/2001 |
| WO | WO01/42443 | 6/2001 |
| WO | WO01/68836 | 9/2001 |
| WO | WO01/75164 | 10/2001 |
| WO | WO01/92513 | 12/2001 |
| WO | WO01/96584 | 12/2001 |
| WO | WO02/44321 | 6/2002 |
| WO | WO 02/059257 A2 | 8/2002 |
| WO | WO 02/059294 A1 | 8/2002 |
| WO | WO 03/046186 A1 | 6/2003 |

OTHER PUBLICATIONS

Kunkel et al. Genes Dev. Feb. 1988;2(2):196-204.*
Good et al. Gene Ther, 1997. 4:45-54.*
Zhao et al., Mol. Cell. 2001, 7:539-549.*
Bertrand et al. 1997, RNA 3: 75-88.*
Elbashir et al. Nature 2001, vol. 411, pp. 494-498.*
Lin, S-L et al., "D-RNAi (Messenger RNA-antisense DNA Interference) as a Novel Defense System Against Cancer and Viral Infections", *Bentham Science*, vol. 1, No. 3, pp. 241-247, 2001.
Miyagishi, M. et al, "U6 promoter-driven siRNAs with four uridine 3' overhangs efficiently suppress targeted gene expression in mammalian cells", *Nature Biotechnology*, vol. 19, No. 5, pp. 497-500, 2002.
Sui, G. et al., "A DNA vector-based RNAi technology to suppress gene expression in mammalian cells", *PNAS*, vol. 99, No. 8, pp. 5515-5520, 2002.
Stünkel et al., "A Nucleosome Positioned in the Distal Promoter Region Activates Transcription of the Human U6 Gene," *Molecular and Cellular Biology*, 17:8, Aug. 1997, pp. 4397-4405.
Lee et al., "Expression of small interfering RNAs targeted against HIV-1 *rev* transcripts in human cells," *Nature Biology*, vol. 19, May 2002, pp. 500-505.
Yu et al., "RNA interference by expression of short-interfering RNAs and hairpin RNAs in mammalian cells," *PNAS*, vol. 99, No. 9, Apr. 30, 2002, pp. 6047-6052.
Sui et al., "A DNA vector-based RNAi technology to suppress gene expression in mammalian cells," PNAS, vol. 99, No. 8, Apr. 16, 2002, pp. 5515-5520.
Brummelkamp et al., "A System for Stable Expression of Short Interfering RNAs in Mammalian Cells," *Science*, vol. 296, Apr. 19, 2002, pp. 550-553.
Paddison et al., "Short hairpin RNAs (shRNAs) induce sequence-specific silencing in mammalian cells," *Genes & Development*, vol. 16, Mar. 8, 2002, pp. 948-958.
Caplen et al., "Specific inhibition of gene expression by small double-stranded RNAs in invertebrate and vertebrate systems," *PNAS*, vol. 98, Aug. 14, 2001, pp. 9742-9747.
Elbashir et al., "Duplexes of 21—nucleotide RNAs mediate RNA interference in cultured mammalian cells," *Nature*, vol. 411, May 24, 2001, pp. 494-498.
Parrish et al., "Functional Anatomy of a dsRNA Trigger: Differential Requirement for the Two Trigger Strands in RNA Interference," *Molecular Cell*, vol. 6, Nov. 2000, pp. 1077-1087.
Kennerdell and Carthew, "Use of dsRNA-Mediated Genetic Interference to Demonstrate that *frizzled* and *frizzled* 2 Act in the Wingless Pathway," *Cell*, vol. 95, Dec. 23, 1998, pp. 1017-1026.
Fire et al., "Potent and specific genetic interference by double-stranded RNA in *Caenorhabditis elegans*," *Nature*, vol. 391, Feb. 19, 1998, pp. 806-811.

* cited by examiner

*Primary Examiner*—Tracy Vivlemore
(74) *Attorney, Agent, or Firm*—DLA Piper US LLP

(57) ABSTRACT

DNA compositions that mediate gene silencing via RNA interference are provided. The DNA compositions include an RNA polymerase III promoter, which drives expression of a nucleotide sequence encoding an intermediate small interfering RNA molecule, and RNA polymerase III terminator.

17 Claims, 7 Drawing Sheets

Linear Cassette

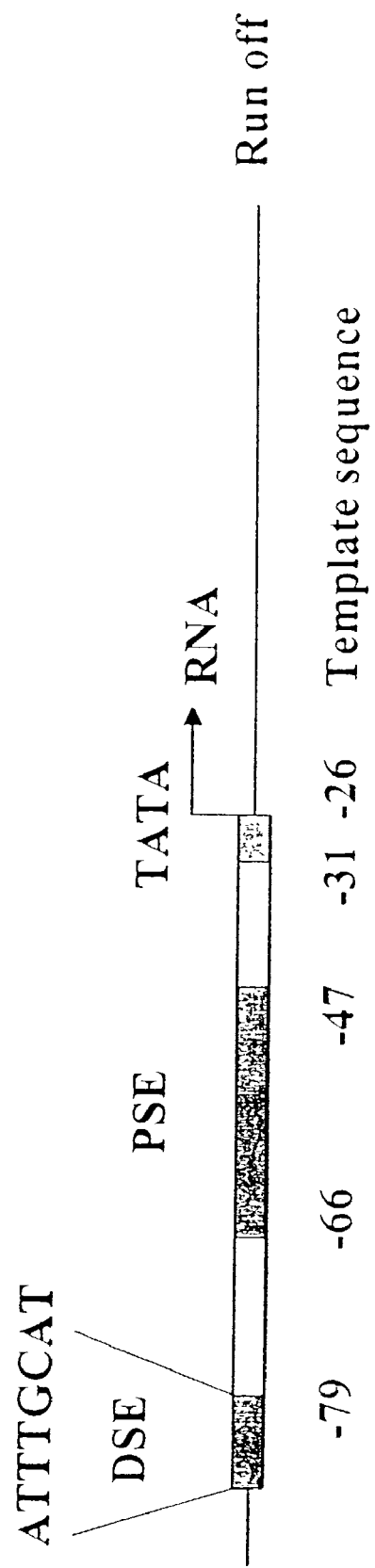
Fig. 1B Linear Cassette

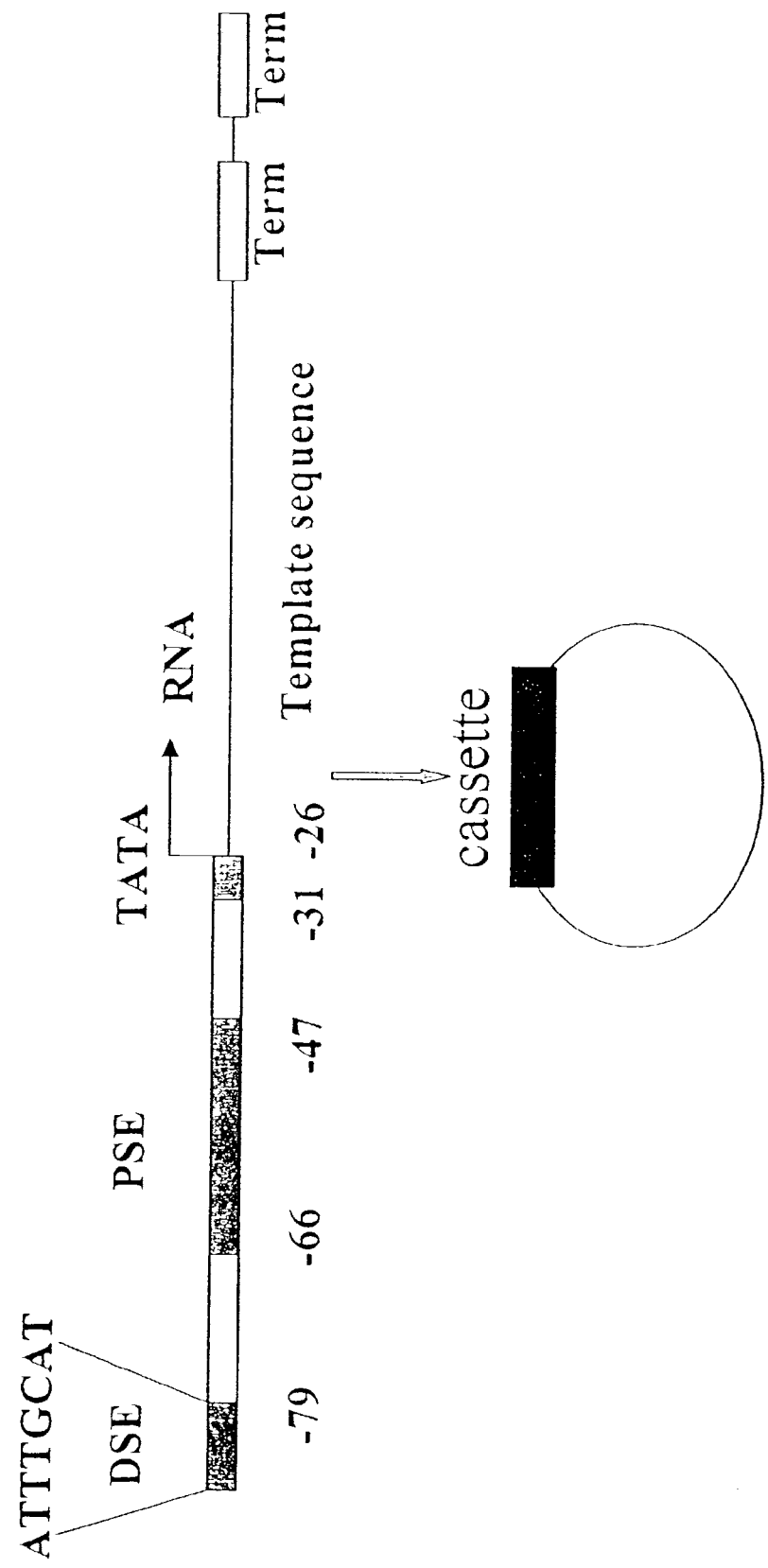
Fig. 2 Linear Cassette

Fig. 3
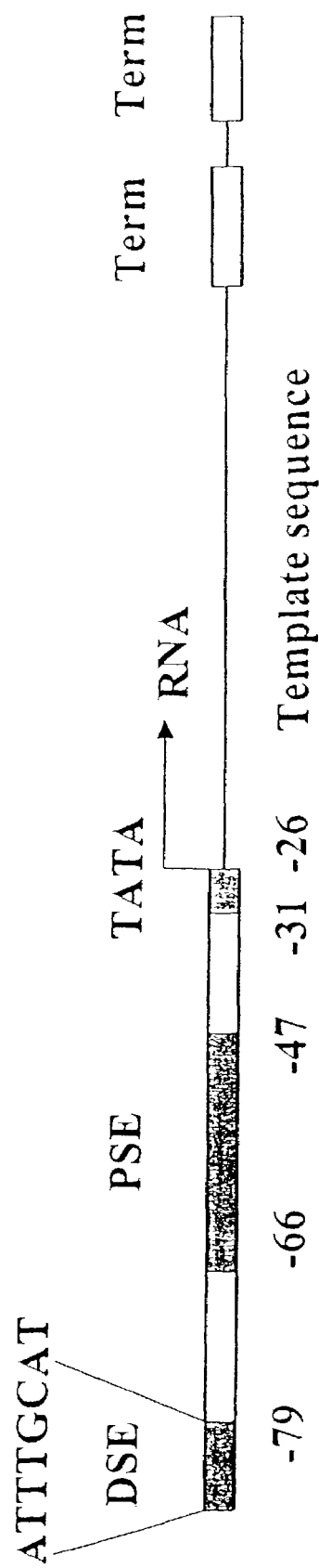
Linear Cassette
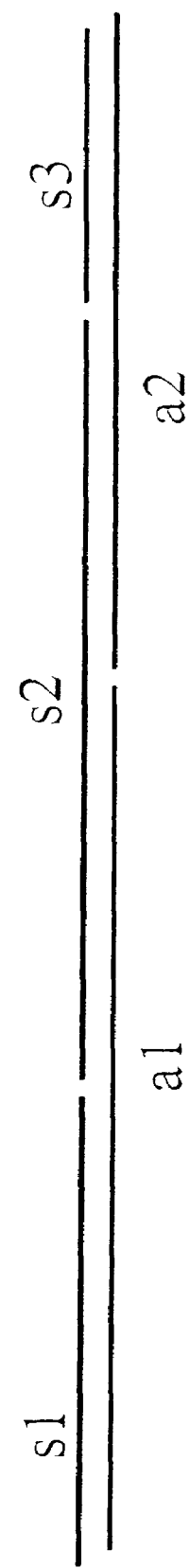
Assembled Linear Cassette

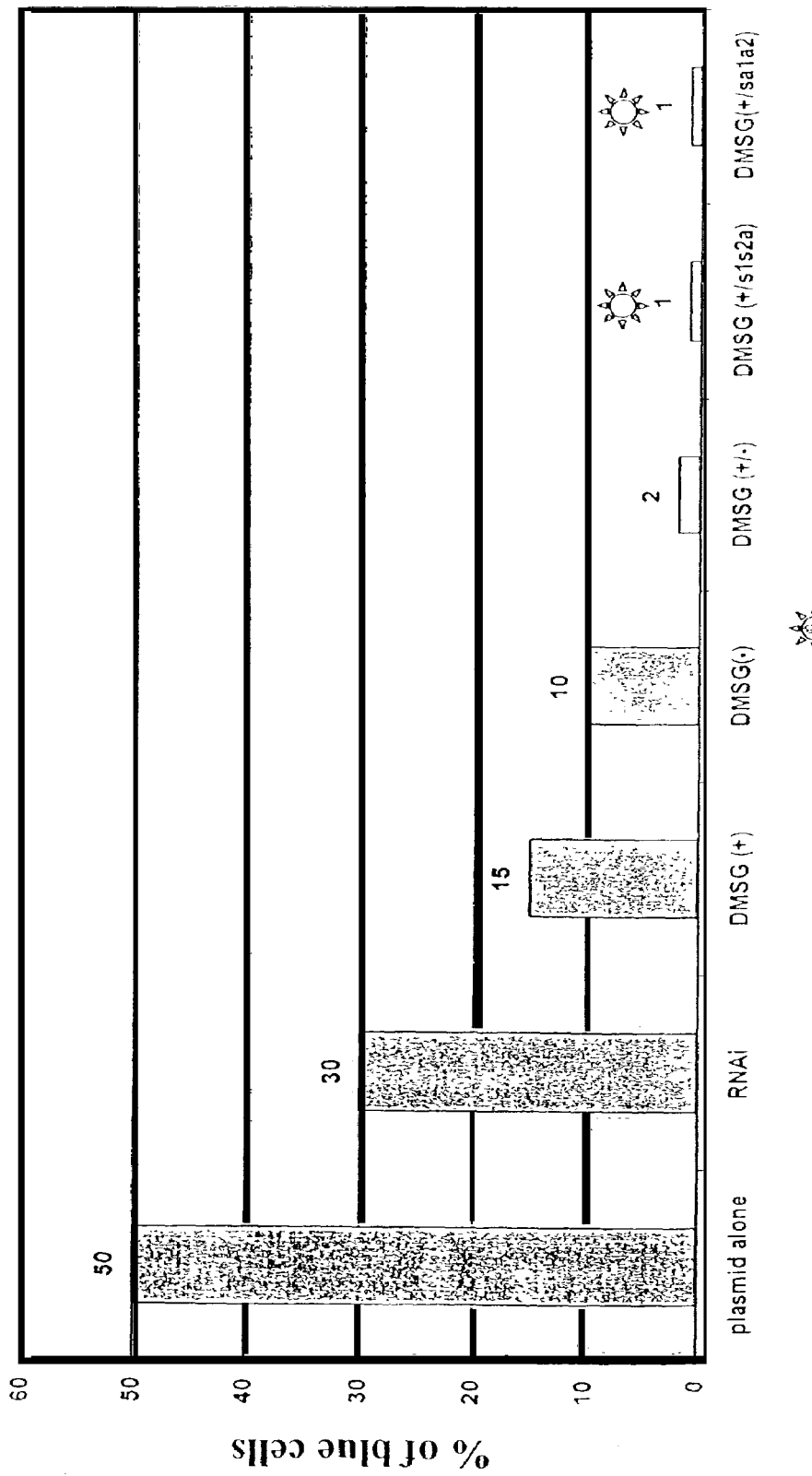
Fig. 4 FITC-labeled DMSG cassettes targeting lacZ

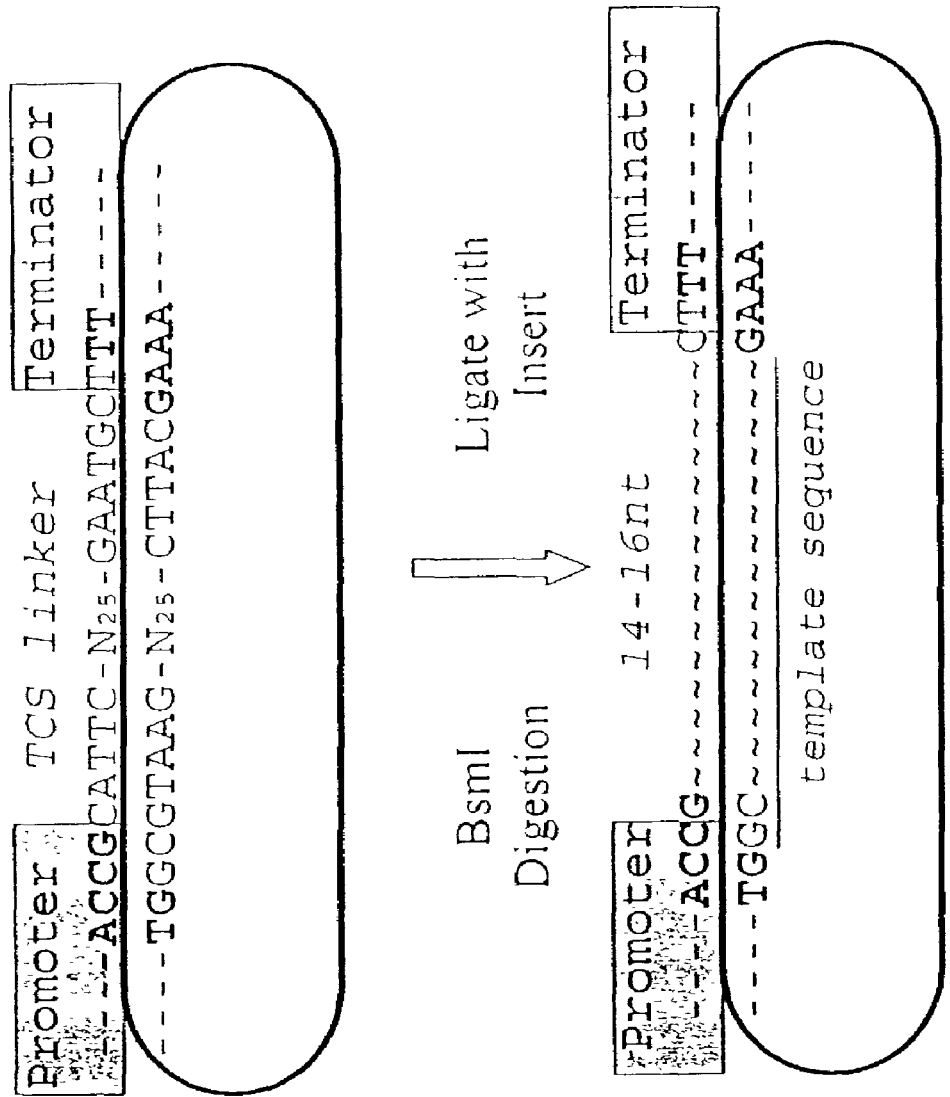
Fig. 5 DMSG Vector

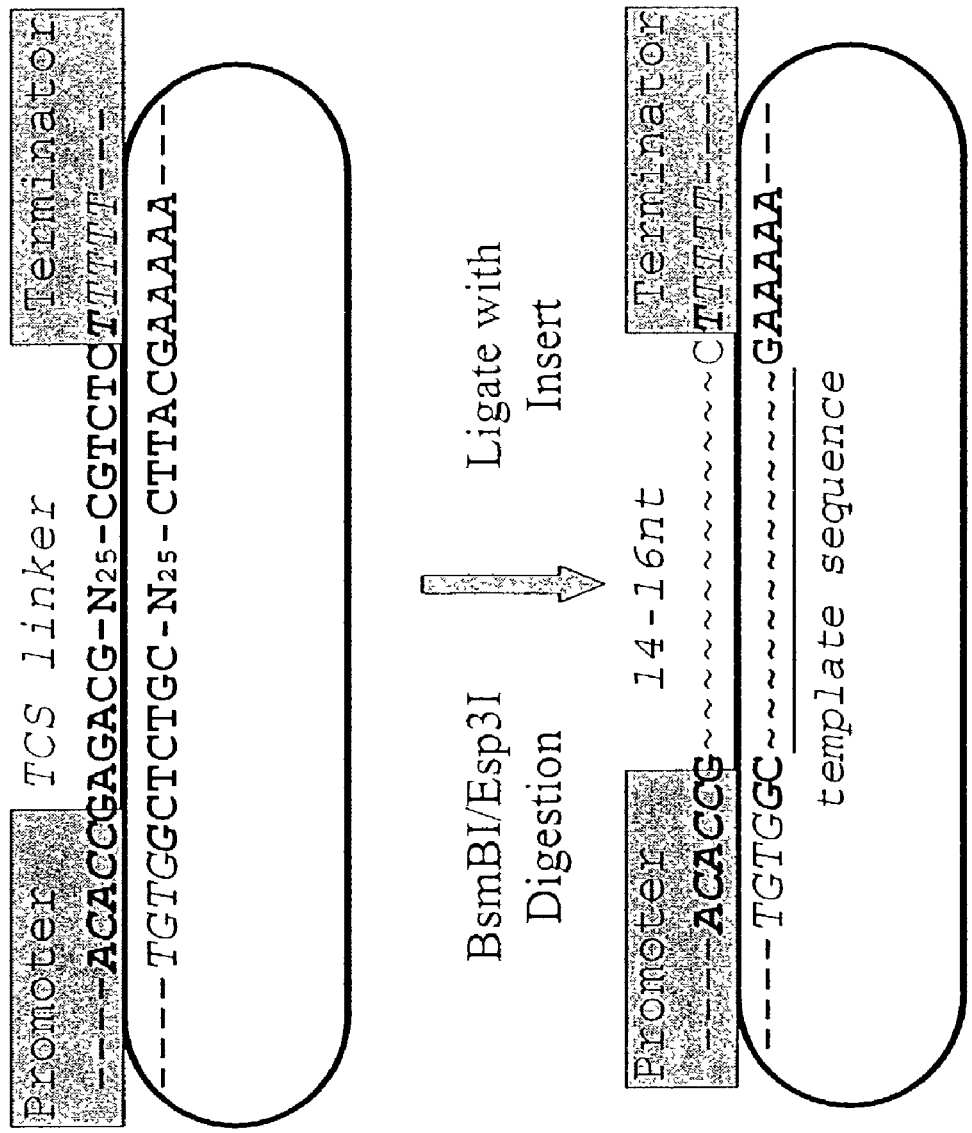
Fig. 6 DMSG Vector

COMPOSITIONS FOR DNA MEDIATED GENE SILENCING

This application is a continuation-in-part of U.S. Ser. No. 10/202,479, filed Jul. 23, 2002, now U.S. Pat. No. 7,294,504, which claims the benefit of priority under 35 U.S.C. § 119(e) to U.S. Ser. No. 60/343,697 filed Dec. 27, 2001, the entire contents of each of which is incorporated herein by reference.

FIELD OF THE INVENTION

The invention relates generally to post-transcriptional gene silencing, and more specifically to DNA mediated post-transcriptional gene silencing by RNA interference.

BACKGROUND OF THE INVENTION

Eliminating the expression of a gene provides researchers with information on the functions of the gene. This can be done at the protein level by inhibiting protein functions with specific inhibitors or at the RNA level by preventing the mRNA from being translated into protein. Traditional methods for RNA level inhibition include antisense oligonucleotide and ribozyme. These methods of suppressing gene expression also provide potential treatments for human diseases.

A recent method of silencing gene expression at the mRNA level, termed RNA interference or RNAi, has emerged to be a very powerful alternative to the previous technologies. It works by a largely unknown yet much more active mechanism than those of antisense. Double-stranded RNA ("dsRNA") is involved in this post-transcriptional gene silencing, a naturally occurring phenomenon in plants and fungi (Cogoni and Macino, Curr Opin Microbiol, 6:657-62. 1999). When introduced into worms, flies, or early mouse embryos, dsRNA induces a cellular response that degrades the mRNA that shares the same sequence with one strand of the dsRNA (Fire, Trends Genet, 9:358-363, 1999). In some systems, a few copies of the dsRNA can induce total degradation of target mRNAs (Fire et al., Nature, 6669:806-811, 1998). RNAi works at a very high success rate with almost any sequence in mRNAs (Caplen et al., *Proc. Natl. Acad. Sci. USA* 17:9742-9747, 2001).

RNAi holds great promise as a gene function study tool, and a potential therapeutic treatment for human diseases if it can be successfully used in mammalian cells or organisms. RNAi in most mammalian systems had been largely unsuccessful until recently because introduction of dsRNA similar to those used in worms and flies induced a general blockage of gene expression by mammalian anti-viral system involving PKR and interferon (Caplen et al., Gene, 1-2:95-105. 2000; Oates et al., Dev Biol, 1:20-8. 2000). However, by using a short, 21-23 nucleotide dsRNA, Elbashir et al. and other researchers showed that small interfering RNA (siRNA) could reduce or knock down specific gene expression without causing a global shut-down (Caplen et al., *Proc. Natl. Acad. Sci. USA* 17:9742-7. 2001; Elbashir et al., Nature, 6836:494-8. 2001).

The use of pol III promoters can effectively result in the production of siRNA inside mammalian cells. For example, an H1-RNA promoter, which, like the U6 promoter, is a class III promoter of pol III, was used on a plasmid vector to direct transcription of a short hairpin RNA that was subsequently processed inside cells to produce siRNAs (Brummelkamp et al., *Science* 296:550-553. 2002). Similarly, the U6 promoter was used to produce short hairpin RNAs (Paddison et al., *Genes Devel.*, 8:948-958. 2002; Paul et al., *Nat. Biotechnol.* 5:505-508. 2002; Sui et al., *Proc. Natl. Acad. Sci. USA* 8:5515-20. 2002; Yu et al., *Proc. Natl. Acad. Sci. USA* 9:6047-6052. 2002), or sense and antisense siRNAs (Lee et al., *Nat. Biotechnol.* 5:500-505, 2002; Miyagishi and Taira, *Nat. Biotechnol.* 5:497-500, 2002; Yu et al., *Proc. Natl. Acad. Sci. USA* 9:6047-52, 2002). Short hairpin RNAs (shRNAs) can mimic the naturally occurring micro-RNAs (miRNAs), which may be related to RNAi. However, current data concerning the design and processing of such artificial shRNAs to function as RNAi inducer remain conflicting. For example, the size (e.g. longer than 7 nucleotide) and sequence of the hairpin loop was found to be very important in one report (Brummelkamp et al., supra, 2002), while shorter loops (1, 4 or 6 nucleotides) were used successfully by others (Paddison et al., supra, 2002; Paul et al., supra, 2002; Sui et al., supra, 2002; Yu et al., supra, 2002). A gene silencing effect was dependent on the order or orientation of the sense and the antisense strands within the hairpin in some cases (Paddison et al., supra, 2002), but marginally important or irrelevant in others (Paul et al., supra, 2002) (Yu et al., *Proc. Natl. Acad. Sci. USA* 9:6047-52. 2002). All of the above studies took advantage of the short class III of pol III promoters and its simple terminator to generate high copy number of short transcripts. A simple natural terminator might be insufficient to stop all transcripts at the desired position, though, as longer transcripts that have the potential of inducing non-specific expression shut down were observed (Lee et al., supra, 2002). Synthetic siRNAs or shRNAs transcribed from U6 promoters were effective in silencing transgenes or viral genes after being delivered by a hydrodynamic transfection method into adult mice (McCaffrey et al., Nature, 418:38-39, 2002).

The method of introducing into cells either long or short dsRNA molecules, isolated from in vitro or in vivo transcription, processing in soluble cell extracts, or chemical synthesis, has serious limitations. One limitation is that isolated dsRNA-mediated gene silencing, also referred to as gene knock-down, is only temporary in the sense that the effects of dsRNA can only last a limited number of cell divisions because the genetic information carried on RNA molecules is not integrated into the chromosome of the host cell. Another limitation is that RNA molecules are notoriously unstable and subject to degradation by environmentally abundant RNases. Therefore, handling RNA molecules demands extreme caution. Use of RNA molecules for therapeutic purpose has been unpractical. Modified RNA, such as adding protection groups to the nucleotides or changing the backbone of the polynucleotide chain, can give improved stability as in many cases involving antisense studies. However, several forms of modified RNA molecules that are more resistant to RNase degradation than natural RNA appeared to have lessened or lost RNAi capability, whereas replacing one strand of dsRNA with DNA did not induce RNAi at all (Parrish et al., *Mol. Cell.* 5:1077-87. 2000). In addition, the expenses for making RNA molecules are high and the process tedious and complicated.

As a result of these limitations, there is great interest in providing materials and methods for gene silencing that can be permanently introduced into cells or organisms (e.g. mammals such as a mouse or a human), and/or does not rely on using RNA molecules as mediators. DNA molecules, on the other hand, are more stable and cost-effective than RNA molecules. DNA molecules can be integrated into a host cell genome and can have long-term effect on the host cell. DNA molecules are relatively easy to synthesize and manipulate.

SUMMARY OF THE INVENTION

Methods and compositions are provided for suppressing the expression of a gene targets and for degrading a target RNA using DNA as a vehicle. The method is referred to as "DNA mediated silencing of a gene" ("DMSG"; "De-message"). As such, the present invention provides gene-specific interference, for example, in a eukaryotic cell or organism, including a mammalian cell or organism, by RNA interference (RNAi) effects in a target cell (i.e., a cell in which a particular RNA is to be degraded). The invention provides the advantage that RNAi can be performed without the need to manipulate RNA molecules outside of a target cell. RNAi can be induced for transient gene knock down, as well as for permanent gene knock down because DNA molecules encoding the RNAi can be inserted into the chromosome of the target cell. Accordingly, DMSG also can be used to generate a genetically modified animal by incorporating the DMSG into the germ line, thus providing generations of animal that express the encoded RNAi, by design, either constitutively or when induced with an inducing agent. As such, another advantage of the present invention is that gene-specific silencing can be restricted to one or a few cell types, or to a particular time, without causing global shut down of the genes in other cells of an organism.

The present invention relates to an isolated deoxyribonucleic acid (DNA) molecule containing an expressible template nucleotide sequence of at least about 16 nucleotides encoding an intermediate small interfering ribonucleic acid (RNA) molecule (siRNA), which mediates RNA interference of a target RNA. In one embodiment, the intermediate siRNA contains a 5' portion having at least about 15 nucleotides complementary to a sense strand of the target RNA, and, optionally, a 3' terminal portion of about 1 to 5 nucleotides, and is designed such that it selectively hybridizes to the sense strand of the target RNA. In another embodiment, the intermediate siRNA contains a 5' portion having at least about 15 nucleotides complementary to an antisense strand of the target RNA, and, optionally, a 3' terminal portion of about 1 to 5 nucleotides, and is designed such that it selectively hybridizes to an antisense strand of a target RNA. In one aspect of the above embodiments, the intermediate siRNA includes a 3' terminal portion of 1 to 5 nucleotides, and in a further aspect, the 3' terminal portion is not complementary to the sense strand or to the antisense strand, respectively, of the target RNA.

The present invention also provides a DNA-mediated silencing of gene expression (DMSG) cassette, which includes an isolated nucleic acid molecule as set forth above operatively linked to at least one heterologous nucleotide sequence. In one embodiment, the DMSG cassette includes, in operative linkage, an RNA polymerase III (pol 111) promoter, an expressible template nucleotide sequence, and at least one pol III terminator, wherein the expressible template nucleotide sequence is heterologous with respect to the pol III promoter, and consists of at least about 16 nucleotides encoding an intermediate siRNA. The siRNA can include a 5' portion of at least about 15 nucleotides, which is complementary to a sense strand of the target RNA, and, optionally, a 3' terminal portion of about 1 to 5 nucleotides, wherein the intermediate siRNA selectively hybridizes to the sense strand of the target RNA; or can include a 5' portion of at least about 15 nucleotides, which is complementary to an antisense strand of the target RNA, and, optionally, a 3' terminal portion of about 1 to 5 nucleotides, wherein the intermediate siRNA selectively hybridizes to the antisense strand of the target RNA. For example, an intermediate siRNA is about 21 to 23 nucleotides in length, which can include a 3' terminal portion of about 1 to 4 nucleotides in length.

The pol III promoter or pol III terminator or both of a DMSG cassette of the invention can be a mammalian U6 gene pol III promoter or pol III terminator, for example, human U6 gene pol III promoter or terminator (or both) or a mouse U6 gene pol III promoter or terminator or both. For example, the DMSG cassette can include, in operative linkage, a sense polynucleotide sequence comprising nucleotides 6 to 13 of SEQ ID NO:1, nucleotide 19 to 38 of SEQ ID NO:1, nucleotides 66 to 69 of SEQ ID NO:1, the template nucleotide sequence, and at least one transcriptional terminator comprising a TTTT tetranucleotide sequence; an antisense polynucleotide, which is complementary the above-described nucleotide sequence; or a double stranded polynucleotide comprising such a sense polynucleotide and antisense polynucleotide, which can selectively hybridize to each other. Where the encoded intermediate siRNA molecules of such a double stranded DMSG include the optional 3' terminal portion of 1 to 5 nucleotides, an siRNA molecule formed upon expression of the DMSG cassette and selective hybridization of the intermediate siRNA molecules contains 3' overhangs of 1 to 5 nucleotides at each strand of a double stranded siRNA. In another embodiment, the DMSG cassette contains an expressible template nucleotide sequence that encodes a first intermediate siRNA, and the expressible template nucleotide sequence further is operatively linked to a second expressible template nucleotide sequence encoding a second intermediate siRNA. In one aspect of this embodiment, the 5' portion of the second intermediate siRNA is complementary to the 5' portion of the first intermediate siRNA, whereby, upon expression, the 5' portion of the first intermediate siRNA selectively hybridizes to the 5' portion of the second intermediate siRNA, thereby forming a hairpin structure.

The transcriptional terminator of a DMSG cassette of the invention can be included a nucleotide sequence of naturally pol III terminator, for example, a human U6 gene terminator comprising SEQ ID NO:48 or a mouse U6 gene terminator comprising SEQ ID NO:49; or can contain a modified pol III terminator designed to terminate pol III transcription at a specific nucleotide, for example a modified pol III terminator such as those set forth as SEQ ID NO:50 or SEQ ID NO:51. In addition, a DMSG cassette can further include an operatively linked enhancer, which can be a constitutively active enhancer or an inducible enhancer.

Where a DMSG cassette is a double stranded DNA molecule, one strand can encode a first intermediate siRNA, which is complementary to the sense strand of the target RNA, and the second strand can encode a second intermediate siRNA, which is complementary to the antisense strand of the target RNA. In one embodiment, the encoded first intermediate siRNA and second siRNA can selectively hybridize to form a double stranded siRNA, which can mediate RNA interference. In another embodiment, such a double stranded siRNA has a 3' overhang of 1 to 5 nucleotides at each 3' terminus. Also provided is a vector containing a DMSG cassette of the invention, as is a cell containing a DMSG cassette, which can be contained in a vector.

The present invention also relates to methods of mediating RNA interference of a target RNA, generally in a cell, by expressing at least one intermediate siRNA, and generally at least a first intermediate siRNA and a second intermediate siRNA, wherein the 5' portions of the first and second intermediate siRNA molecules selectively hybridize with each other. Thus, the present invention relates to methods of mediating RNA interference of a target RNA in a cell, for example, by introducing at least one DMSG cassette into the cell, whereby expression of an siRNA including the intermediate siRNA encoded by the DMSG cassette triggers degradation of the target RNA, thereby mediating RNA interference in the cell. In addition, the invention provides methods of knocking down expression of a target gene in a sample, for example, by contacting the sample with at least one DMSG cassette, wherein expression of an siRNA including the intermediate siRNA encoded by the DMSG cassette triggers degradation of a target RNA molecule encoded by the target gene, thereby knocking down expression of the target gene in the sample.

The present invention also relates to methods of tracking, among a population of cells, a specific cell or specific group of cells subject to DNA mediated gene silencing. Such a method can be performed, for example, by introducing at least one detectably labeled DMSG cassette into the specific cell or into each cell of the specific group of cells; and detecting the detectable label, thereby tracking, among the population of cells, the specific cell or specific group of cells. In addition, the invention relates to a method of identifying a cell subject to DNA mediated gene silencing, for example, by contacting at least one cell with at least one detectably labeled DMSG cassette, under conditions sufficient for introduction of a DMSG cassette into a cell; and detecting the presence of the detectable label in a cell.

The present invention also relates to a method of assessing the function of a gene in a test cell. Such a method can be performed, for example, by introducing at least one DMSG cassette into the test cell, and observing a phenotype of the test cell upon expression of an siRNA including the intermediate siRNA encoded by the DMSG cassette, whereby a comparison of the phenotype of the test cell as compared to a control cell is indicative of a function of the target gene, thereby assessing the function of the gene in the test cell.

In addition, the invention relates to a method of determining whether an agent effects or affects a specific gene, particularly expression of a specific gene, in a test cell. Such a method can be performed, for example, by expressing an siRNA including an intermediate siRNA encoded by at least one DMSG cassette in the test cell, wherein an intermediate siRNA of the siRNA includes a 5' portion complementary to an RNA molecule encoded by the specific gene in the test cell, contacting the test cell and a control cell with the agent, and comparing a phenotype of the test cell with that of the control cell, thereby assessing whether the agent effects or affects the specific gene in the test cell.

The present invention also relates to a method of ameliorating an RNA mediated disorder in an individual by inducing RNAi against the target RNA mediating the disorder. Such a method can be performed, for example, by contacting cells of the individual that exhibit the RNA mediated disorder with at least one DMSG cassette, wherein expression of an siRNA comprising one or more intermediate siRNA molecules encoded by the template nucleotide sequence of DMSG cassette can mediate RNAi against the target RNA. The cells of the individual can be contacted with the DMSG cassette ex vivo, then administered back into the subject, or the DMSG can be administered to the subject such that it contacts the cells containing the target RNA in vivo. The target RNA can be an endogenous RNA, including a coding RNA (e.g., mRNA) or a non-coding RNA (e.g., an X-chromosome modifier or structural RNA), or can be an exogenous RNA, for example, a bacterial or viral RNA present in the cell due to infection of the individual.

The present invention also relates to a kit, which includes at least one isolated DNA molecule comprising an expressible template nucleotide sequence and/or at least one DMSG cassette. Also provided a non-human transgenic organism, which is genetically modified to contain a DMSG cassette in its genome.

The present invention also provides an isolated modified U6 gene promoter, particularly a shortened enhancer, including a DSE operatively linked to a PSE (compare naturally occurring U6 gene 5' upstream regulatory sequence; SEQ ID NO:36). A modified U6 gene enhancer of the invention is exemplified by 5'-ATTGCAT-N(10-60)-CTTACCGTAACT-TGAAAGTA-3' (SEQ ID NO:38), and by 5'-ATTGCAT-N(10-60)-CTCACCCTAACTGTAAAGTA-3' (SEQ ID NO:39), wherein N(10-60) indicates that any 10 to 60 nucleotides can be positioned between the DSE (ATTGCAT) and the PSE (human, SEQ ID NO:34; or mouse, SEQ ID NO:35, as shown). Such a modified U6 gene enhancer is exemplified by a DSE and PSE separated by about 10 nucleotides—5'-ATTGCAT-N(13)-CTTACCGTAACTTGAAAGTA-3' (SEQ ID NO:40); and 5'-ATTGCAT-N(13)-CTCACCCTAACTG-TAAAGTA-3' (SEQ ID NO:41)—and more particularly by nucleotides 6 to 46 of SEQ ID NO:1. In one embodiment, a shortened U6 gene enhancer is operatively linked to a promoter element, particularly a TATA element. In another embodiment, the modified enhancer, which can be operatively linked to a promoter, is contained in a vector, which can include a template cloning site in operative linkage. In addition, the present invention provides a modified mammalian U6 gene pol III terminator, for example, the modified pol III terminators exemplified by SEQ ID NOS:50 and 51.

BRIEF DESCRIPTION OF THE DRAWINGS

FIGS. 1A and 1B are schematic representations of two DMSG cassettes in linear formats. The enhancer, promoter, template sequence, two terminator sequences ("Term"; "TM") in the DMSG-TM cassette (FIG. 1A) or the abrupt end of a run-off ("RO"; FIG. 1B) cassette are shown.

FIG. 2 is a schematic representation of a DMSG cassette in a circular (e.g., plasmid) format.

FIG. 3 is a schematic representation of a DMSG cassette in an assembled linear format (see Example 3). Oligonucleotides are represented as thick lines forming a double stranded ("ds") DNA with nicks.

FIG. 4 is a graph demonstrating a DMSG effect on lacZ expression (see Example 4). siRNA was included as control. DMSG cassettes encoding only the plus strand, only the minus strand, or both strands, were used to silence reporter gene expression. In the last two experiments the DMSG plus cassette was co-transfected with assembled minus cassette, with either the sense DNA (s1s2) or antisense DNA (a1a2) synthesized as two oligonucleotides. The 3' base of each of s2 and a2 is labeled with fluorescein isothiocyanate (FITC).

FIG. 5 is a drawing showing a DMSG cassette on a vector, pDMSG1 (see Example 6). The top of the figure represents a plasmid, with sequences around the template cloning site ("TCS linker"; SEQ ID NO: 44) shown. The bottom depicts the insertion of template sequence into the cloning sites (see, also, SEQ ID NO: 45).

FIG. 6 is show a DMSG cassette on a second vector, pDMSG2, which is similar to pDMSG1 (FIG. 5) except that it contains a restriction endonuclease recognition site that leaves a 4 nucleotide overhang (see Example 6). The top of the figure represents a plasmid, with sequences around the template cloning site ("TCS linker", SEQ ID NO: 46) shown. The bottom depicts the insertion of template sequence into the cloning sites (see, also, SEQ ID NO: 47).

DETAILED DESCRIPTION OF THE INVENTION

Figure 1A:
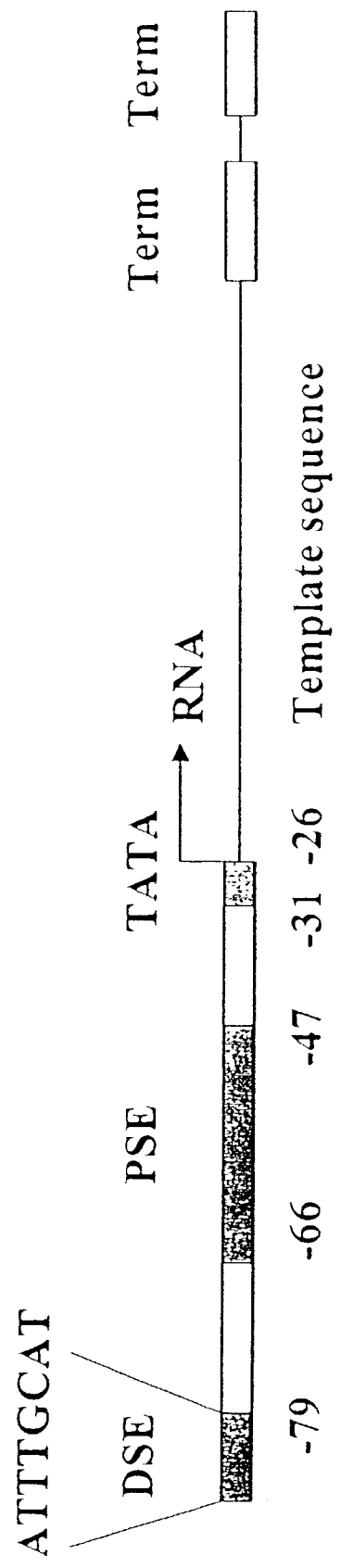

RNA interference (RNAi) is a post-transcriptional gene silencing process that is induced by a dsRNA (a small interfering RNA; siRNA), and has been used to modulate gene expression. Generally, RNAi has been performed by contacting cells with a double stranded siRNA. However, manipulation of RNA outside of cell is tedious due to the sensitivity of RNA to degradation. The present invention obviates the need for manipulating RNA by providing deoxyribonucleic acid (DNA) compositions encoding small interfering RNA (siRNA) molecules, or intermediate siRNA molecules, comprising one strand of an siRNA. Accordingly, the present invention provides an isolated DNA molecule, which includes an expressible template nucleotide sequence of at least about 16 nucleotides encoding an intermediate siRNA, which, when a component of an siRNA, mediates RNA interference (RNAi) of a target RNA.

An intermediate siRNA is a ribonucleotide sequence that, in one embodiment, includes a 5' portion, which includes at least about 15 nucleotides complementary to a sense strand or an antisense strand of a target RNA, and a 3' terminal portion, including about 1 to 5 nucleotides that are not complementary to the sense strand or antisense strand, respectively, of the target RNA, wherein the siRNA complementary to the sense strand of the target RNA can selectively hybridize to the sense strand of the target RNA, and wherein a first intermediate siRNA complementary to a sense strand of a target RNA sequence and a second intermediate siRNA complementary to the antisense strand of the same target RNA sequence can selectively hybridize to each other. In another embodiment, an siRNA includes a 5' portion, which includes at least about 15 nucleotides complementary to a sense strand or an antisense strand of a target RNA, and, optionally, a 3' terminal portion, which, when present, is about 1 to 5 nucleotides in length and can, but need not, be complementary to the sense strand or antisense strand, respectively, of the target RNA, wherein, the siRNA complementary to the sense strand of the target RNA can selectively hybridize to the sense strand of the target RNA, and wherein a first intermediate siRNA complementary to a sense strand of a target RNA sequence and a second intermediate siRNA complementary to the antisense strand of the same target RNA sequence can selectively hybridize to each other. Where two siRNA molecules, each comprising a 3' terminal region, selectively hybridize to form a double stranded siRNA, the siRNA contains 3' overhangs at each end.

As used herein, the term "template" or "template nucleotide sequence" refers to a nucleotide sequence of a DNA molecule of the invention (or of a DMSG cassette; see below) that encodes a ribonucleotide sequence that contains a 5' portion complementary to the sense strand or the antisense strand of a target RNA, and, optionally, a 3' terminal portion that can, but need not, be complementary to the sense or antisense strand, respectively, of the target nucleotide sequence. As such, a template nucleotide sequence encodes an intermediate siRNA, which comprises a strand of a double stranded siRNA.

The term "intermediate", when used in reference to an siRNA, means one strand, either the sense or antisense strand or a portion thereof, of a double stranded siRNA. For convenience of discussion, the terms "sense" strand (or "plus" strand) and "antisense" strand (or "minus" strand) are used herein as they relate, for example, to an mRNA molecule, wherein the sense (plus) strand contains the information for encoding a peptide and an antisense (minus) strand would be complementary thereto. It should be recognized that, in fact, an antisense mRNA sequence is generally not produced in a cell. However, it should be further recognized that an siRNA need not necessarily be directed against an mRNA molecule but can be directed against any RNA molecule, including any endogenous or exogenous RNA in a cell or sample. For example, an siRNA can be directed against a structural RNA molecule such as a ribosomal RNA or small nuclear RNA (snRNA) molecules such as those involved in a spliceosome complex; a nucleotide sequence of transcribed intron, as occurs in a heterogeneous nuclear RNA (hnRNA); an X-chromosome modifier; or a microRNA; or can be directed against a nucleotide sequence of an RNA virus or of an RNA form of a DNA virus (which comprises a plus strand and a minus strand), including a coding or non-coding RNA sequence; or an RNA expressed from a bacterium, which can be symbiotic with a host containing the bacterium or can be an infectious bacterium, particularly a disease causing bacterium.

An intermediate siRNA generally is about 16 to 30 nucleotides in length, usually about 20 to 25 nucleotides in length, and particularly 21, 22 or 23 nucleotides in length. For convenience of discussion, reference is made to a 5' portion and a 3' terminal portion of an intermediate siRNA. The term "5' portion" refers to the nucleotide sequence (which generally is about 15 to 29 nucleotides in length, generally about 18 to 25, and particularly about 20 to 23 nucleotides in length) of an intermediate siRNA that is complementary to a sense or antisense sequence of the target RNA; the term "3' terminal portion" refers to an optional nucleotide sequence (which, when present, generally is 1 to 5 nucleotides in length, particularly 2, 3 or 4 nucleotides in length) of an intermediate siRNA that includes the 3' terminal nucleotide. Generally, an siRNA includes a 3' terminal portion such that, upon selective hybridization of an intermediate siRNA with a complementary siRNA to form an siRNA, 3' terminal portion of the intermediate siRNA forms a 3' overhang. For purposes of discussion of the compositions of the invention, reference is made generally herein to a template nucleotide sequence containing a 3' terminal portion of about 1 to 5 nucleotides that are not complementary to the corresponding sequences of the target RNA. As such, it should be recognized that an isolated DNA molecule of the invention does not encompass, for example, any isolated nucleotide sequence or restriction fragment of a naturally occurring polynucleotide (e.g., a gene sequence), and that a DMSG cassette of the invention does not encompass any such nucleotide sequence linked to any heterologous nucleotide sequence.

An isolated DNA molecule of the invention can be single stranded or double stranded. Where the isolated DNA molecule is single stranded, it can encode a sense or antisense intermediate siRNA; or can encode both a sense and an antisense intermediate siRNA, which, upon expression, can selectively hybridize to form an siRNA. Where the isolated DNA molecule is double stranded, it can encode a sense or antisense intermediate siRNA on one strand; or can encode on one strand both a sense and an antisense intermediate siRNA, which, upon expression, can selectively hybridize to form an siRNA; or can encode sense intermediate siRNA on one strand and an antisense intermediate siRNA on the second strand, which, upon expression, can selectively hybridize to form an siRNA. An isolated DNA molecule of the invention also can encode two or more intermediate siRNA molecules, two or more of which can selectively hybridize to each other to form an siRNA, or can be specific for two or more different target RNA molecules.

An isolated DNA molecule also can be a linear DNA molecule, which has a first end and a second end, or can be circular. In addition, the isolated DNA molecule can be in a free form, for example, in solution, in a freeze dried form, or in a precipitate; or can be contained in a vector, for example, an expression vector. Such an isolated DNA, which can, but need not, be in a vector, also can be contained in a cell, for example, a host cell, a target cell, or a genetically modified cell containing the DNA molecule integrated in its genome.

The present invention also provides a plurality of isolated DNA molecules. As used herein, the term "plurality", when used in reference to DNA molecules, DMSG cassettes, or siRNA or intermediate siRNA molecules, means two or more (e.g., 2, 3, 4, 5, 6, 7, 8, etc.) different molecules, including two or more different populations of such molecules. As such, a plurality of DNA molecules of the invention includes at least two such isolated DNA molecules. For example, a plurality can include a first isolated DNA molecule encoding an intermediate siRNA that includes a 5' portion complementary to the sense strand of the target RNA; and at least a second isolated DNA molecule of the invention (e.g., a second; a second and a third; a second, a third and a fourth; etc.). It should be recognized that the terms "first", "second", "third", and the like are used only to distinguish different isolated DNA molecules of the invention and not, for example, to refer to an order or an importance or other such characteristic.

Where a plurality of the invention includes a first isolated DNA molecule encoding an intermediate siRNA that includes a 5' portion complementary to the sense strand of the target RNA (a "first intermediate siRNA"), the plurality also can contain, for example, at least a second isolated DNA molecule encoding a second intermediate siRNA that contains a 5' portion complementary to the antisense strand of the target RNA to which the first intermediate siRNA is directed, wherein, upon expression, the first and second intermediate siRNA molecules can selectively hybridize to form an siRNA. Alternatively, or in addition, the plurality can include at least a second (or third) isolated DNA molecule that encodes an intermediate siRNA including a 5' portion complementary to a sense strand of a second target RNA, and can further include at least a third (or fourth) isolated DNA molecule of the plurality encodes an intermediate siRNA including a 5' portion complementary to an antisense strand of the second target RNA.

A plurality of isolated DNA molecules also can include a first isolated DNA molecule encoding an intermediate siRNA having a 5' portion complementary to an antisense strand of the target RNA of a target RNA; and at least a second isolated DNA molecule encoding an intermediate siRNA having a 5' portion complementary to the sense strand of the target RNA, wherein the encoded first and second intermediate siRNA molecules can, but need not, be complementary to each other such that, upon expression, they can selectively hybridize to form an siRNA. Additional combinations of components such as those encoding intermediate siRNA molecules directed to one or more other target RNA molecules or to other regions of a first target RNA also are contemplated.

As disclosed herein, a DNA molecule of the invention encodes an expressible template nucleotide sequence. The term "expressible", when used in reference to a template nucleotide sequence, means that the template nucleotide sequence can be transcribed into an RNA molecule, particularly an intermediate siRNA. As such, an expressible template nucleotide sequence generally is, or can be, operatively linked to one or more transcriptional regulatory elements, including, for example, one or more promoters, which comprise a transcription start site; enhancers or silencers, which increase or decrease, respectively, the level of transcription of an expressible nucleotide sequence; silencers; or terminators, which comprise a transcription stop site.

Accordingly, the present invention also provides DNA-mediated silencing of gene (DMSG) cassettes, which include an isolated DNA molecule of the invention (which encodes an intermediate siRNA) operatively linked to at least one heterologous nucleotide sequence. The heterologous nucleotide sequence can be, for example, one or more operatively linked transcriptional regulatory elements such as a promoter, enhancer, terminator, or combination thereof; a cloning site such as a restriction endonuclease recognition site, a recombinase recognition site, a topoisomerase recognition site, or a combination thereof; or one or more other moieties. For example, a DMSG cassette of the invention can include, in operative linkage, a promoter, a template nucleotide sequence encoding an intermediate siRNA, and a terminator, and can further include an enhancer. Such a DMSG cassette is exemplified herein by a DMSG cassette comprising a template nucleotide sequence operatively linked to human U6 gene enhancer, promoter and terminator elements, which direct transcription by RNA polymerase III (pol III). In addition, the DMSG cassette can be contained in a vector, and two or more DMSG cassettes, which can be the same or different, can be operatively linked together, and can be linear or circular and can, but need not, be contained in a vector.

Promoters and enhancers, which can be used to drive transcription of a sense intermediate siRNA or an antisense intermediate siRNA, can be constitutive (e.g., a viral promoter such as a cytomegalovirus promoter or an SV40 promoter), inducible (e.g., a metallothionein promoter), repressible, tissue specific, developmental stage specific, or the like. Thus, for example, two different inducible promoters can be used to drive transcription of a sense intermediate siRNA and an antisense intermediate siRNA. In such an instance, promoter activation can be used to induce production of a sense intermediate siRNA, an antisense intermediate siRNA, or both, as desired. Furthermore, the transcriptional regulatory element can be selected such that they direct transcription by a eukaryotic RNA polymerase I, II or III (pol I, II or III) or by a prokaryotic RNA polymerase such as an $\alpha$-pol, $\beta$-pol or $\gamma$-pol. Regulatory elements such as a eukaryotic pol III promoter, enhancer and terminator, for example, those present in the human U6 gene, can be particularly useful for expressing an intermediate siRNA because the pol III generates a large number of copies of a transcript.

As used herein, the term "operatively linked" means that a regulatory element is positioned with respect to an expressible nucleotide sequence such that the element can effect its regulatory activity. A transcriptional regulatory element having enhancer activity, for example, can be located at some distance, including adjacent to or up to thousands of nucleotides away from, and upstream or downstream from a promoter and a nucleotide sequence to be transcribed, and still exert a detectable enhancing effect on the level of expression of an encoded reporter molecule. Transcriptional regulatory element, including eukaryotic and prokaryotic promoters, terminators, enhancers, and silencers, are well known in the art and can be chemically synthesized, obtained from naturally occurring nucleic acid molecules, or purchased from commercial sources.

Promoters include, for example, those from cytomegalovirus, Moloney leukemia virus, and herpes virus, as well as those from the genes encoding metallothionein, skeletal actin, phosphoenolpyruvate carboxylase, phosphoglycerate, dihydrofolate reductase, and thymidine kinase, as well as promoters from viral long terminal repeats (LTRs) such as Rous sarcoma virus LTR. Enhancers include, for example, constitutively active enhancers such as an immunoglobulin enhancer, or inducible enhancers such as SV40 enhancer; and the like. A metallothionein promoter is a constitutively active promoter that also can be induced to a higher level of expression upon exposure to a metal ion such as copper, nickel or cadmium ion. In comparison, a tetracycline (tet) inducible promoter is an example of a promoter that is induced upon exposure to tetracycline, or a tetracycline analog, but otherwise is inactive. A transcriptional regulatory element also can be a tissue specific regulatory element, for example, a muscle cell specific regulatory element, such that expression of an encoded product is restricted to the muscle cells in an individual, or to muscle cells in a mixed population of cells in culture, for example, an organ culture. Muscle cell specific regulatory elements including, for example, the muscle creatine kinase promoter (Sternberg et al., *Mol. Cell. Biol.* 8:2896-2909, 1988, which is incorporated herein by reference) and the myosin light chain enhancer/promoter (Donoghue et al., *Proc. Natl. Acad. Sci., USA* 88:5847-5851, 1991, which is incorporated herein by reference) are well known in the art. Other tissue specific promoters, as well as regulatory elements only expressed during particular developmental stages of a cell or organism are well known in the art.

Such regulatory element can be either constitutive or regulatable (i.e., inducible or derepressible). Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, recA, lacZ, LacI, and gal promoters of *E. coli*, the α-amylase (Ulmanen et al., *J. Bacteriol.* 162:176-182, 1985) and the sigma-28-specific promoters of *B. subtilis* (Gilman et al., *Gene* 32:11-20, 1984), the promoters of the bacteriophages of *Bacillus* (Gryczan, In: The Molecular Biology of the Bacilli (Academic Press, Inc., NY 1982)), *Streptomyces* promoters (Ward et al., *Mol. Gen. Genet.* 203:468-478, 1986), and the like. Exemplary prokaryotic promoters are reviewed by Glick (*J. Ind. Microbiol.* 1:277-282, 1987); Cenatiempo (*Biochimie* 68:505-516, 1986); and Gottesman (*Ann. Rev. Genet.* 18:415-442, 1984).

A transcriptional regulatory element such as a promoter or an enhancer can be a constitutively active element, which maintains expression of an operatively linked expressible nucleotide sequence at a relatively constant level of activity, or can be an inducible regulatory element. Constitutively active regulatory elements include, for example an actin promoter such as an actin 2 promoter, or an elongation factor (EF) promoter such as an EF1α promoter, each of which is active in a wide variety of different cell types; or can be a tissue specific regulatory element, which is expressed only in one or a few specific cell types, or a developmental phase specific regulatory element, which is expressed only during particular development or growth of an organism. The term "tissue specific" or "developmental phase specific", when used in reference to a regulatory element, particularly a promoter or an enhancer, means a nucleotide sequence that directs transcription in only one or a few cell types, or only during one or a few stages during the growth, development or differentiation of a cell type or an organism, respectively.

As used herein, the term "inducible regulatory element" means a regulatory element that, when exposed to an inducing agent, effects an increased level of transcription of an operatively linked nucleotide sequence, particular a template nucleotide sequence encoding an intermediate siRNA, as compared to the level of transcription, if any, in the absence of an inducing agent. Inducible regulatory elements can be those that have no basal or constitutive activity and only effect transcription upon exposure to an inducing agent, or those that effect a basal or constitutive level of transcription, which is increased upon exposure to an inducing agent. Inducible regulatory elements that effect a basal or constitutive level of expression generally are particularly useful where the induced level of transcription is substantially greater than the basal or constitutive level of expression, for example, at least about two-fold greater, or at least about five-fold greater. Particularly useful inducible regulatory elements do not have a basal or constitutive activity, or increase the level of transcription at least about ten-fold greater than a basal or constitutive level of transcription associated with the regulatory element.

The term "inducing agent" is used to refer to a chemical, biological or physical agent that effects transcription from an inducible regulatory element. In response to exposure to an inducing agent, transcription from the inducible regulatory element generally is initiated de novo or is increased above a basal or constitutive level of expression. Such induction can be identified using the methods disclosed herein, including detecting an increased level of mRNA encoding the bioluminescent polypeptide. The use of an inducible regulatory element in a recombinant nucleic acid molecule of the invention provides a means to express the bioluminescent polypeptide only at a desired time, thus preventing extraneous transcriptional or translational activity in the plant cell.

An inducing agent useful for regulating expression of a particular inducible element is selected based on the particular inducible regulatory element. For example, the inducible regulatory element can be a metallothionein (MT) regulatory element such as an MT2B regulatory element, a copper inducible regulatory element, or a tetracycline inducible regulatory element, the transcription from which can be effected in response to various metal ions, to copper or to tetracycline, respectively (Furst et al., *Cell* 55:705-717, 1988; Mett et al., *Proc. Natl. Acad. Sci., USA* 90:4567-4571, 1993; Gatz et al., *Plant J.* 2:397-404, 1992; Roder et al., *Mol. Gen. Genet.* 243:32-38, 1994, each of which is incorporated herein by reference). The inducible regulatory element also can be an ecdysone regulatory element or a glucocorticoid regulatory element, the transcription from which can be effected in response to ecdysone or other steroid (Christopherson et al., *Proc. Natl. Acad. Sci., USA* 89:6314-6318, 1992; Schena et al., *Proc. Natl. Acad. Sci., USA* 88:10421-10425, 1991, each of which is incorporated herein by reference). In addition, the regulatory element can be a cold responsive regulatory element or a heat shock regulatory element, the transcription of which can be effected in response to exposure to cold or heat, respectively (Takahashi et al., *Plant Physiol.* 99:383-390, 1992, which is incorporated herein by reference).

The term "operatively linked" also is used herein to refer to a cloning site such as a restriction endonuclease or recombinase recognition site, in which case the term means that the cloning site is positioned on a first nucleotide sequence, e.g., a template nucleotide sequence, such that a second nucleotide sequence can be joined thereto and effect its function with respect to the first nucleotide sequence. For example, a first nucleotide sequence, e.g., an expressible template nucleotide sequence, can contain a cloning site operatively linked thereto, such that a second or more nucleotide sequence(s), e.g., a promoter and a terminator, which has a similar cloning site(s), can be joined to the first nucleotide sequence, through the cloning site, wherein each component of the linked unit maintains its function and the two or more linked units function together. Similarly, an expression vector containing an enhancer, promoter, and terminator can contain a template cloning site positioned between the promoter and terminator elements such that a template nucleotide sequence containing compatible termini can be operatively inserted into the cloning site, i.e., inserted such that expression of the template nucleotide sequence is regulated by the enhancer, promoter and terminator (see, for example, FIGS. 5 and 6). The modular nature of the compositions of the invention are particularly suitable to the production of kits containing components that conveniently allow the operative linkage, including insertion, substitution or deletion, of one or more different or combinations of regulatory elements, detectable labels, targeting moieties, and the like such that the expressible template nucleotide sequence can be expressed in one or more particular cell types, as desired.

Restriction endonuclease recognition sites, and their corresponding restriction endonucleases, are well known in the art and commercially available. Restrictions sites useful in the compositions of the invention include those that leave 3' or 5' overhangs, such that operative linkage of two or more nucleotide sequences having the sites is facilitated. Where, for example, a template nucleotide sequence is flanked by restriction sites such that a promoter and a terminator can be operatively linked thereto, the use of different restriction sites at each end of the template can facilitate operative linkage of the promoter and the terminator in the proper position and orientation with respect to the nucleotide sequence encoding the intermediate siRNA such that the linkage can be performed in a single reaction mixture. Recombinase recognition sites also are well known in the art and include, for example, the lox recognition site, linkage of which is effected by the Cre recombinase, att sequences, linkage of which is effected by lambda Int and IHF proteins.

The term "operatively linked" also is used herein with respect to a DNA molecule comprising a template nucleotide sequence, for example, a DMSG cassette, and a molecule attached thereto, in which case the term means that the linkage is such that the functions of the DNA molecule or DMSG cassette and the molecule are maintained. Thus, the DNA molecule or DMSG cassette can be operatively linked to a detectable label or other moiety such as a polynucleotide, peptide, peptidomimetic, small organic molecule or the like that confers a desirable property on the DNA molecule or DMSG cassette. For example, a DMSG can be operatively linked to a moiety such as a cell compartmentalization domain, which can target the DMSG cassette into a cell or to a particular cell compartment. Cell compartmentalization domains are well known in the art and include, for example, a plasma membrane localization domain, a nuclear localization signal, a mitochondrial membrane localization signal, an endoplasmic reticulum localization signal, or the like, or a protein transduction domain such as the human immunodeficiency virus TAT protein transduction domain, which can facilitate translocation of a peptide linked thereto into a cell (see Schwarze et al., Science 285:1569-1572, 1999; Derossi et al., J. Biol. Chem. 271:18188, 1996; Hancock et al., EMBO J. 10:4033-4039, 1991; Buss et al., Mol. Cell. Biol. 8:3960-3963, 1988; U.S. Pat. No. 5,776,689 each of which is incorporated herein by reference).

A detectable label, which facilitates identification of a composition of the invention or of a sample or cell containing the composition, can be a peptide, polypeptide, or chemical or small organic or inorganic molecule that can be conveniently detected. For example, a detectable label can be a molecule such as a biotin, which can be detected using avidin or streptavidin; a fluorescent compound (e.g., Cy3, Cy5, Fam, fluorescein, or rhodamine); a radionuclide (e.g., sulfur-35, technicium-99, phosphorus-32, or tritium); a paramagnetic spin label (e.g., carbon-13); a bioluminescent such as luciferin; an enzyme such as alkaline phosphatase; or a chemiluminescent compound. If desired, a fluorescent compounds such as AAN, JOE, FAM, or TET, alone or in combination with a quencher such as BHQ (see, for example, Molecular Probes, Eugene) can be used to perform a fluorescence resonance energy transfer (FRET) reaction, thereby allowing, for example, detection of formation of a hairpin siRNA, which can be expressed from a DMSG cassette as disclosed herein.

Methods of operatively linking a detectable label or other moiety to a nucleotide sequence are well known in the art (see, for example, Hermanson, "Bioconjugate Techniques" (Academic Press 1996), which is incorporated herein by reference). In addition to providing a means, for example, to detect a cell containing a DMSG cassette, a detectable label or other moiety also can be used to isolate such a cell. For example, where the DMSG comprises a fluorescent compound, cells containing the DMSG cassette readily can be isolated from cells that do not contain the cassette by a methods such as fluorescent activated cell sorting (FACS). Similarly, where the detectable label is a peptide tag such as a myc epitope, FLAG epitope, or the like, an antibody or other binding partner specific for the tag, which itself can be labeled, can be used to isolate or otherwise identify the DMSG cassette, including, for example, a cell containing the cassette.

A DMSG cassette, or two or more linked DMSG cassettes, can be in the form of linear expression cassettes or circular expression cassettes, either of which can, but need not, comprise vector sequences. Furthermore, the DMSG cassette(s), which can be in a vector, can further be in a cell, which can be a host cell useful for maintaining and/or expanding the DMSG cassette, and can be free in the cell or can be integrated into genomic DNA of the cell.

An isolated DNA molecule or a DMSG cassette of the invention can be contained in a vector, which can facilitate manipulation of the nucleic acid molecule, including introduction into a target cell. The vector can be a cloning vector, which is useful for maintaining the DNA molecule of DMSG cassette, or can be an expression vector, which contains regulatory elements useful for expressing the polynucleotide and, where appropriate or desired, for translation of a peptide encoded by a nucleotide sequence linked to the DNA molecule or DMSG cassette or a nucleotide sequence of the vector. An expression vector can contain the expression elements necessary to achieve, for example, sustained transcription of an expressible template nucleotide sequence encoding an intermediate siRNA, or the regulatory elements can be operatively linked to the template nucleotide sequence prior to its being cloned into the vector, i.e., by construction all or a portion of a DMSG cassette.

An expression vector (or the polynucleotide) generally contains or encodes a promoter sequence, which can provide constitutive or, if desired, inducible or tissue specific or developmental stage specific expression of the encoding polynucleotide, a poly-A recognition sequence or other transcription termination site, other transcriptional regulatory elements such as an enhancer, which can be tissue specific, and, where desired, a ribosome recognition site or internal ribosome entry site. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993; each of which is incorporated herein by reference).

Viral expression vectors can be particularly useful for introducing, for example, one or a plurality of DMSG cassettes, which can be on the same or different vectors, into a cell, particularly a cell in a subject. Viral vectors provide the advantage that they can infect host cells with relatively high efficiency and can infect specific cell types. The viral vector also can be derived from a virus that infects cells of an organism of interest, for example, vertebrate host cells such as mammalian, avian or piscine host cells. Viral vectors can be particularly useful for introducing a DMSG cassette into a target cell for practicing a method of the invention. Viral vectors have been developed for use in particular host systems, particularly mammalian systems and include, for example, retroviral vectors, other lentiviral vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980-990, 1992; Anderson et al., Nature 392:25-30 Suppl., 1998; Verma and Somia, *Nature* 389:239-242, 1997; Wilson, *New Engl. J. Med.* 334:1185-1187, 1996, each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide such as a DMSG cassette, which can be contained in a vector, can be introduced into a cell by any of a variety of methods known in the art (Sambrook et al., "Molecular Cloning: A laboratory manual" (Cold Spring Harbor Laboratory Press 1989); Ausubel et al., "Current Protocols in Molecular Biology", John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

DMSG cassettes of the invention are exemplified herein by "run off" DMSG cassettes, which lack a transcriptional terminator element (see FIG. 1B), such as DMSG cassette sequences directed to a plus strand (e.g., a coding strand) of a target RNA (e.g., as set forth in SEQ ID NOS:1 and 2) or a minus strand (e.g., a non-coding strand) of a target RNA (e.g., as set forth in SEQ ID NOS:5 and 6; see, also, Example 1). In addition, DMSG cassettes of the invention are exemplified by DMSG cassette sequences containing one or more transcriptional terminators (see FIG. 1A), such as a DMSG cassette directed to a plus strand of a target RNA (SEQ ID NOS:3 and 4) or a minus strand of a target RNA (SEQ ID NOS:7 and 8; see, also, Example 1). Although the exemplified DMSG cassettes comprise template nucleotide sequences directed to target sense and antisense strands of a green fluorescent protein (GFP), it will be recognized that the present invention encompasses a template nucleotide sequence encoding an intermediate siRNA directed to RNA molecules encoded by any gene or cDNA or the like, or to any target RNA molecule.

Accordingly, the present invention provides, for example, a DMSG cassette, which contains, in operative linkage, a sense polynucleotide sequence comprising nucleotides 6 to 13 of SEQ ID NO:1, nucleotide 27 to 46 of SEQ ID NO:1, nucleotides 66 to 69 of SEQ ID NO:1, and a template nucleotide sequence of at least about 16 nucleotides encoding an intermediate siRNA; an antisense polynucleotide complementary to the above described sense polynucleotide; or a double stranded polynucleotide formed by hybridization of the above described sense and antisense polynucleotides. Such a DMSG cassette can lack a terminator (see, for example, FIG. 1B), or can further include, in operative linkage, at least one transcriptional terminator, for example, in the sense polynucleotide, at least one tetra-thymidine (TTTT) or at least one penta-thymidine (TTTTT) sequence; or in the antisense polynucleotide, at least one tetra-adenosine (AAAA) or at least one penta-adenosine (AAAAA) nucleotide sequence.

It is noted that the natural sequence of the human U6 gene terminator includes a penta-thymidine sequence (TTTTT), of which the first two thymidine residues overlap with the last two Ts of the coding sequence (see SEQ ID NO:48). Because siRNA molecules are most efficient when the 3' terminal portion includes a UU overhang, and pol III transcription generally terminates following the second or third thymidine of the penta-thymidine terminator sequence, transcription of a DMSG cassette as disclosed provides a means to generate nearly perfect siRNA molecules.

In many cases, it can be desirable to express two DMSG cassettes, for example, in a cell, such that a sense and an antisense intermediate siRNA can selectively hybridize to form a functional double stranded siRNA. However, a DMSG cassette also can be constructed such that both a sense and an antisense intermediate siRNA are produced, including, in one embodiment, where the sense and antisense intermediate siRNA sequences comprise a single transcript, wherein the sense and antisense sequences can selectively hybridize to form a hairpin structure that can be processed into a functional double stranded siRNA. Accordingly, the present invention also provides a DMSG cassette, which includes a first template nucleotide sequence encoding a first intermediate siRNA, and wherein the heterologous nucleotide sequence of the DMSG cassette includes a second expressible template nucleotide sequence of at least about 16 nucleotides encoding a second intermediate siRNA, wherein the 5' portion of the second intermediate siRNA is complementary to the 5' portion of the first intermediate siRNA, whereby, upon expression, the 5' portion of the first intermediate siRNA selectively hybridizes to the 5' portion of the second intermediate siRNA to form a hairpin structure. Such a DMSG cassette can further include at least one RNA polymerase III transcriptional regulatory element, for example, at least one human U6 gene transcriptional regulatory element such as a promoter, enhancer, terminator, or combination thereof.

In view of the present disclosure, it will be recognized that the compositions of the invention, particularly DMSG cassettes, can be integrated into a cell genome and, therefore, can be useful for generating genetically modified cells, or transgenic non-human organisms comprising such cells. Such genetically modified cells and transgenic non-human organisms can be useful, for example, as animal models for a disease characterized by reduced or a lack of expression of a gene, or as tools to identify agents useful for effecting expression of a gene. For example, a transgenic rodent such as a transgenic mouse, rat, or hamster, or other transgenic animal such as a transgenic sheep or goat or other experimental animal, can be prepared such that one or more target genes is knocked down due to expression from a DMSG cassette of an siRNA specific for the target gene, and the transgenic non-human organism can be examined directly to determine the effect produced by the gene knock down, and to examine the effect of agent suspected of being able to ameliorate the effect due to the gene knock down in the organism. Although transgenic organisms are exemplified herein by transgenic non-human animals, it should be recognized that transgenic plants comprising one or more DMSG cassettes also are contemplated.

Various methods are known for producing a transgenic animal. In one method, an embryo at the pronuclear stage (a "one cell embryo") is harvested from a female and the transgene is microinjected into the embryo, in which case the transgene will be chromosomally integrated into the germ cells and somatic cells of the resulting mature animal. In another method, embryonic stem cells are isolated and the transgene is incorporated into the stem cells by electroporation, plasmid transfection or microinjection; the stem cells are then reintroduced into the embryo, where they colonize and contribute to the germ line. Methods for microinjection of polynucleotides into mammalian species are described, for example, in U.S. Pat. No. 4,873,191, which is incorporated herein by reference. In yet another method, embryonic cells are infected with a retrovirus containing the transgene, whereby the germ cells of the embryo have the transgene chromosomally integrated therein.

When the animals to be made transgenic are avian, microinjection into the pronucleus of the fertilized egg is problematic because avian fertilized ova generally go through cell division for the first twenty hours in the oviduct and, therefore, the pronucleus is inaccessible. Thus, the retrovirus infection method is preferred for making transgenic avian species (see U.S. Pat. No. 5,162,215, which is incorporated herein by reference). If microinjection is to be used with avian species, however, the embryo can be obtained from a sacrificed hen approximately 2.5 hours after the laying of the previous laid egg, the transgene is microinjected into the cytoplasm of the germinal disc and the embryo is cultured in a host shell until maturity (Love et al., *BioTechnology* 12, 1994). When the animals to be made transgenic are bovine or porcine, microinjection can be hampered by the opacity of the ova, thereby making the nuclei difficult to identify by traditional differential interference-contrast microscopy. To overcome this problem, the ova first can be centrifuged to segregate the pronuclei for better visualization.

Non-human transgenic animals can be murine, bovine, porcine, ovine, avian or other animals. The transgene can be introduced into embryonal target cells at various developmental stages, and different methods are selected depending on the stage of development of the embryonal target cell. The zygote is the best target for microinjection. The use of zygotes as a target for gene transfer has a major advantage in that the injected DNA can incorporate into the host gene before the first cleavage (Brinster et al., *Proc. Natl. Acad. Sci., USA* 82:4438-4442, 1985). As a consequence, all cells of the transgenic non-human animal carry the incorporated transgene, thus contributing to efficient transmission of the transgene to offspring of the founder, since 50% of the germ cells will harbor the transgene.

A transgenic animal can be produced by crossbreeding two chimeric animals, each of which includes exogenous genetic material within cells used in reproduction. Twenty-five percent of the resulting offspring will be transgenic animals that are homozygous for the exogenous genetic material, 50% of the resulting animals will be heterozygous, and the remaining 25% will lack the exogenous genetic material and have a wild type phenotype.

In the microinjection method, the transgene is digested and purified free from any vector DNA, for example, by gel electrophoresis. The transgene can include an operatively associated promoter, which interacts with cellular proteins involved in transcription, and provides for constitutive expression, tissue specific expression, developmental stage specific expression, or the like. Such promoters include those from cytomegalovirus (CMV), Moloney leukemia virus (MLV), and herpes virus, as well as those from the genes encoding metallothionein, skeletal actin, phosphoenolpyruvate carboxylase (PEPCK), phosphoglycerate (PGK), dihydrofolate reductase (DHFR), and thymidine kinase (TK). Promoters from viral long terminal repeats (LTRs) such as Rous sarcoma virus LTR also can be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements, including, for example, enhancer elements to stimulate transcription, splice acceptors, termination and polyadenylation signals, ribosome binding sites to permit translation, and the like.

In the retroviral infection method, the developing non-human embryo can be cultured in vitro to the blastocyst stage. During this time, the blastomeres can be targets for retroviral infection (Jaenich, *Proc. Natl. Acad. Sci, USA* 73:1260-1264, 1976). Efficient infection of the blastomeres is obtained by enzymatic treatment to remove the zona pellucida (Hogan et al., "Manipulating the Mouse Embryo" (Cold Spring Harbor Laboratory Press, 1986). The viral vector system used to introduce the transgene is typically a replication-defective retrovirus carrying the transgene (Jahner et al., *Proc. Natl. Acad. Sci., USA* 82:6927-6931, 1985; Van der Putten et al., *Proc. Natl. Acad. Sci, USA* 82:6148-6152, 1985). Transfection is easily and efficiently obtained by culturing the blastomeres on a monolayer of virus producing cells (Van der Putten et al., supra, 1985; Stewart et al., *EMBO J.* 6:383-388, 1987). Alternatively, infection can be performed at a later stage. Virus or virus-producing cells can be injected into the blastocoele (Jahner et al., *Nature* 298:623-628, 1982). Most of the founders will be mosaic for the transgene since incorporation occurs only in a subset of the cells which formed the transgenic nonhuman animal. Further, the founder can contain various retroviral insertions of the transgene at different positions in the genome, which generally will segregate in the offspring. In addition, it is also possible to introduce transgenes into the germ line, albeit with low efficiency, by intrauterine retroviral infection of the mid-gestation embryo (Jahner et al., supra, 1982).

Embryonal stem cell (ES) also can be targeted for introduction of the transgene. ES cells are obtained from pre-implantation embryos cultured in vitro and fused with embryos (Evans et al. *Nature* 292:154-156, 1981; Bradley et al., *Nature* 309:255-258, 1984; Gossler et al., *Proc. Natl. Acad. Sci., USA* 83:9065-9069, 1986; Robertson et al., Nature 322:445-448, 1986). Transgenes can be efficiently introduced into the ES cells by DNA transfection or by retrovirus mediated transduction. Such transformed ES cells can thereafter be combined with blastocysts from a nonhuman animal. The ES cells thereafter colonize the embryo and contribute to the germ line of the resulting chimeric animal (see Jaenisch, *Science* 240:1468-1474, 1988).

The present invention also provides a plurality of DMSG cassettes, including at least two of the DMSG cassettes of the invention. The expressible template nucleotide sequence of a first DMSG cassette of the plurality can encode a first intermediate siRNA including a 5' portion complementary to the sense strand of the target RNA. Such a first DMSG cassette can comprise, in a plurality, at least a second DMSG, wherein the expressible template nucleotide sequence of a second DMSG cassette, for example, encodes a second intermediate siRNA including a 5' portion complementary to the antisense strand of the target RNA. In one embodiment, the 5' portion of a first intermediate siRNA encoded by the expressible template nucleotide sequence of a first DMSG cassette can be complementary to the 5' portion of the second intermediate siRNA, wherein selective hybridization of the first and second intermediate siRNA molecules forms an active siRNA, which can mediate RNAi.

In another embodiment, the expressible template nucleotide sequence of at least a second DMSG cassette of the plurality encodes a second intermediate siRNA including a 5' portion complementary to a sense strand of a second target RNA. In a further embodiment, the expressible template nucleotide sequence of at least a second DMSG cassette of the plurality encodes a second intermediate siRNA including a 5' portion complementary to an antisense strand of a second target RNA, whereby the first and second encoded intermediate siRNA molecules can selectively hybridize to form a function double stranded siRNA.

Also provided is a plurality of DMSG cassettes wherein the expressible template nucleotide sequence of a first DMSG cassette of the plurality encodes an intermediate siRNA including a 5' portion complementary to the antisense strand of the target RNA, and wherein the expressible template nucleotide sequence of at least a second DMSG cassette of the plurality encodes an siRNA including a 5' portion complementary to the sense strand of the target RNA. In a still further embodiment, the present invention provides a plurality of DMSG cassettes, wherein the 5' portion of the siRNA encoded by the first DMSG cassette is complementary to the 5' portion of the siRNA encoded by the second DMSG cassette. In still further embodiments, the expressible template nucleotide sequence of at least a second DMSG cassette of the plurality encodes an siRNA comprising a 5' portion complementary to an antisense strand of a second target RNA, and the expressible template nucleotide sequence of at least a second DMSG cassette of the plurality encodes an siRNA comprising a 5' portion complementary to a sense strand of a second target RNA.

As disclosed herein, the compositions of the invention are useful for mediating RNAi by targeting one or more RNA molecules, which can be ribosomal RNA molecules, mRNA molecules, viral RNA molecules, or the like. Accordingly, the present invention provides methods of mediating RNA interference (RNAi) of a target RNA in a cell. Such a method can be performed by introducing at least one DMSG cassette into the cell, whereby expression of an siRNA comprising the intermediate siRNA encoded by the at least one DMSG cassette triggers degradation of the target RNA, thereby mediating RNA interference in said cell. In one embodiment, the at least one DMSG cassette encodes an intermediate siRNA complementary to a sense strand of the target RNA. In another embodiment, at least two DMSG cassettes are introduced into the cell, wherein a first DMSG cassette of the at least two DMSG cassettes encodes a first intermediate siRNA comprising a 5' portion complementary to a sense strand of a target RNA, and wherein a second DMSG cassette of the at least two DMSG cassettes encodes a second intermediate siRNA comprising a 5' portion complementary to an antisense strand of the target RNA. In a further embodiment, the 5' portion of the first intermediate siRNA complementary to the sense strand of the target RNA is complementary to the 5' portion of the second intermediate siRNA complementary to the antisense strand of the target RNA, whereby the first intermediate siRNA and the second intermediate siRNA selectively hybridize to form a siRNA.

As disclosed herein, a target RNA can be any RNA molecule present in a sample or a cell, including an endogenous or exogenous RNA and a coding or non-coding RNA. For example, where an RNA virus has infected a cell, an siRNA can be designed such that it targets a coding or non-coding portion of the RNA virus, thereby mediating RNAi of the viral RNA. A target RNA also can be an snRNA, an hnRNA, or an mRNA molecule, whereby the siRNA can knock down expression of a target gene encoding the hnRNA and mRNA, or preventing processing of an hnRNA to an mRNA. As such, it should be recognized that a method of the invention can be used to mediate RNAi of an RNA molecule expressed from an endogenous gene in a cell or of an exogenous RNA molecule. Accordingly, the present invention also provides a method of knocking down expression of a target gene in a sample or cell by RNAi. As used herein, the term "knock down", when used in reference to an effect of RNAi on gene expression, means that the level of gene expression is inhibited, or is reduced to a level below that generally observed when examined under substantially the same conditions, but in the absence of RNAi.

A method of knocking down gene expression can be performed, for example, by contacting a sample with at least one DMSG cassette according to the invention, wherein expression of an siRNA including the intermediate siRNA encoded by the DMSG cassette triggers degradation of a target RNA molecule encoded by the target gene, thereby knocking down expression of the target gene in the sample. The target gene can be an endogenous gene or can be an exogenous gene that is introduced into the cell and is maintained in the cell transiently or stably.

A sample useful for practicing such a method can be a reaction mixture, wherein the RNAi is performed in vitro using substantially purified reagents such as purified target RNA molecules, which can be isolated naturally occurring RNA molecules (e.g., RNA molecules in a cell extract), or can be chemically synthesized or recombinantly generated RNA molecules, and enzymes including, for example, an appropriate RNA polymerase and, if necessary, other factors required for expression of the intermediate siRNA molecules. For example, the reaction mixture can be a coupled in vitro transcription/translation reaction, wherein an siRNA comprising an intermediate siRNA encoded by a DMSG cassette can decrease the amount of translation product generated. The sample also can be a cell sample, which can be an isolated cell such as a cell in culture, or cells of a tissue or organ sample of an organism, or cells in situ in an organism. Where the sample comprises a cell, the DMSG cassette can be contacted with the cell such that the DMSG cassette is introduced into the cell, whereby the encoded intermediate siRNA can be expressed. Where the cell is in situ in an organism, the DMSG cassette can be targeted to the particular cell or population of cells, for example, by administering a composition containing the cassette to the site of the cell(s) or into a blood vessel that provides circulation to the cell(s).

A method of knocking down expression of a target gene can be performed, for example, by contacting at least two DMSG cassettes with the sample, for example, by introduction into a cell containing the target gene, wherein a first DMSG cassette of the at least two DMSG cassettes encodes a first intermediate siRNA including a 5' portion complementary to a sense strand of a target RNA (encoded by the target gene), and wherein a second DMSG cassette of the at least two DMSG cassettes encodes a second intermediate siRNA including a 5' portion complementary to an antisense strand of the target RNA. In another embodiment, the 5' portion of the first intermediate siRNA complementary to the sense strand of the target RNA is complementary to the 5' portion of the second intermediate siRNA complementary to the antisense strand of the target RNA, whereby the first intermediate siRNA and the second intermediate siRNA selectively hybridize to form a siRNA.

The present invention also relates to a method of ameliorating an RNA mediated disorder in an individual by inducing RNAi against the target RNA mediating the disorder. As used herein, reference to an "RNA mediated disorder" means a pathologic condition characterized by the presence of an RNA molecule that is involved in the signs or symptoms associated with the condition. By way of example, an RNA mediated disorder can be a genetic disorder, wherein a mutation or other change of an endogenous gene results in production of an mRNA that encodes an aberrant polypeptide. An RNA mediated disorder also is exemplified by a bacterial infection, wherein an RNA expressed from the infecting bacterium encodes a polypeptide that has a deleterious effect on the infected individual. A method of the invention can ameliorate such RNA mediated disorders by reducing or inhibiting expression of the aberrant polypeptide or bacterial polypeptide, respectively. An RNA mediated disorder is further exemplified by a viral infection, wherein an RNA expressed from the virus encodes a polypeptide required for replication and/or infectiousness of the virus. A method of the invention can ameliorate an RNA mediated disorder due to such an infecting virus by reducing or inhibiting replication and/or spread of the virus. In view of the these examples, it will be recognized that various disorders can be ameliorated according to a method of the invention.

A method of ameliorating an RNA mediated disorder can be performed, for example, by contacting cells of an individual that exhibits (or is susceptible to) the RNA mediated disorder with at least one DMSG cassette, wherein expression of an siRNA comprising one or more intermediate siRNA molecules encoded by the template nucleotide sequence of DMSG cassette can mediate RNAi against the target RNA. The individual can be any organism suffering from such a disorder, including a vertebrate organism, for example, a mammalian organism such as a domesticated animal such as a pet or a commercially important animal such as a bovine, equine, porcine, or ovine animal, and particularly a human.

The cells of the individual can be contacted with the DMSG cassette ex vivo, then administered back into the subject. Such a method can be useful, for example, for a heterozygous type disorder such as sickle cell anemia, where the disorder is due to a mutation of one or both hemoglobin genes, and where an individual heterozygous for the disorder expresses a normal hemoglobin protein and a defective hemoglobin protein. By obtaining bone marrow cells from such a heterozygous individual, contacting the cell ex vivo with a DMSG cassette encoding an siRNA directed to the mutant RNA sequence, and re-introducing the cells back into the patient, wherein expression of the aberrant hemoglobin molecule will be knocked down. If desired, the DMSG cassette can be operatively linked to a fluorescent compound such that bone marrow cells that contain the DMSG cassette can be selected. An advantage of such a method is that, while white blood cell precursors, as well as red blood cell precursors, in the population of bone marrow cells are genetically modified to contain the DMSG cassette, any expression of the encoded siRNA should have little if any effect in mature white blood cells derived from such genetically modified white blood cell precursor because the white blood cells do not express the hemoglobin gene.

Cells of an individual also can be contacted with a DMSG cassette by administering the DMSG cassette to the subject such that it contacts the cells containing the target RNA in vivo. The target RNA can be an endogenous RNA, including a coding RNA (e.g., hnRNA or mRNA) or a non-coding RNA (e.g., an X-chromosome modifier, or other structural or functional RNA such as an snRNA), or can be an exogenous RNA, for example, a bacterial or viral RNA present in the cell due to infection of the individual. An advantage of a method of in vivo gene therapy of the invention is that an aberrant RNA or an RNA that is not normally expressed in cells of the individual is targeted and, therefore, it is not important to consider the effect, for example, of a DMSG cassette entering and being expressed in a normal (healthy) cell because an siRNA comprising an intermediate siRNA encoded by the DMSG has no effect in a cell lacking the target RNA.

For administration to an individual, the DMSG cassette generally is formulated in a composition suitable for administration to the individual. Thus, the invention also provides compositions that contain at least one DMSG cassette and are suitable for administration to a living individual. As such, a DMSG cassette is useful as a medicament for treating a subject suffering from an RNA mediated disorder.

Pharmaceutically acceptable carriers for preparing a composition for administration to an individual are well known and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the DMSG cassette. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. It will be recognized that the choice of a pharmaceutically acceptable carrier, including a physiologically acceptable compound, depends, for example, on the route of administration of the composition, which can be, for example, orally or parenterally such as intravenously, and by injection, intubation, topical application, or other such method known in the art. The composition containing the DMSG cassette, or a plurality of DMSG cassettes, also can contain a second reagent such as a diagnostic reagent, nutritional substance, toxin, or therapeutic agent, for example, a cancer chemotherapeutic agent where the DMSG cassette is being administered to treat a cancer (e.g., by knocking down expression of an oncogene such as Ras or p53).

The DMSG cassette can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a composition useful for practicing a method of the invention, and other "masked" liposomes similarly can be used, such liposomes extending the time that the DMSG cassette remains in the circulation. Cationic liposomes, for example, also can be modified with specific receptors or ligands (Morishita et al., *J. Clin. Invest.*, 91:2580-2585, 1993, which is incorporated herein by reference). In addition, a DMSG cassette can be introduced into a cell using, for example, adenovirus-polylysine DNA complexes (see, for example, Michael et al., *J. Biol. Chem.* 268:6866-6869, 1993, which is incorporated herein by reference).

A composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of an RNA mediated disorder, for example, intravenously or intra-arterially into a blood vessel supplying a tumor.

The total amount of a DMSG cassette to be administered in practicing a method of the invention can be administered to a subject as a single dose, either as a bolus or by infusion over a relatively short period of time, or can be administered using a fractionated treatment protocol, in which multiple doses are administered over a prolonged period of time. It will be recognized that the amount of the pharmaceutical composition to treat an RNA mediated disorder in an individual depends on many factors including the age and general health of the subject as well as the route of administration and the number of treatments to be administered. In view of these factors, the skilled artisan would adjust the particular dose as necessary. In general, the formulation of the composition and the routes and frequency of administration are determined, initially, using Phase I and Phase II clinical trials.

The composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The invention also provides methods of tracking, among a population of cells, a specific cell or specific group of cells subject to DNA mediated gene silencing. Such a method can be performed, for example, by introducing at least one DMSG cassette, which includes a detectable label, into the specific cell (or into each cell of the specific group of cells), and detecting the detectable label, thereby tracking, among the population of cells, the specific cell or specific group of cells subject to DNA mediated gene silencing. In one embodiment, a first DMSG cassette and a second DMSG cassettes are introduced into the specific cell or specific group of cells, wherein the first DMSG cassette encodes a first intermediate siRNA comprising a 5' portion complementary to a sense strand of a target RNA, wherein the second DMSG cassette encodes a second intermediate siRNA comprising a 5' portion complementary to an antisense strand of the target RNA, and wherein the 5' portion of the first intermediate siRNA encoded by the first DMSG cassette is complementary to the 5' portion of the second intermediate siRNA.

The invention also provides methods of identifying a cell subject to DNA mediated gene silencing. Such a method can be performed, for example, by contacting at least one cell with at least one DMSG cassette, which is operatively linked to a detectable label, under conditions sufficient for introduction of a DMSG cassette into a cell, and detecting the detectable label of the at least one DMSG cassette in a cell. In one embodiment, the method includes contacting the at least one cell with a first DMSG cassette and a second DMSG cassette, wherein the first DMSG cassette encodes a first intermediate siRNA comprising a 5' portion complementary to a sense strand of a target RNA, wherein the second DMSG cassette encodes a second intermediate siRNA comprising a 5' portion complementary to an antisense strand of the target RNA, and wherein the 5' portion of the first intermediate siRNA encoded by the first DMSG cassette is complementary to the 5' portion of the second intermediate siRNA. In a further embodiment of this invention method, the detectable label of the first DMSG cassette is different from the detectable label of the second DMSG cassette, and the detecting step comprises detecting the detectable label of the first DMSG cassette and/or the detectable label of the second DMSG cassette. Where both the first and second detectable labels are identified in a single cell, the cell is identified as a cell subject to DNA mediated gene silencing. Methods of tracking and/or identifying a cell containing a DMSG cassette comprising a detectable label provide a means for selecting cells that contain one or more DMSG cassettes, or for identifying cells that contain one or more DMSG cassettes following administration of the DMSG cassettes (or cells) to a subject.

The invention also provides a method for assessing the function of a gene in a test cell. Such a method can be performed, for example, by introducing at least one DMSG cassette into the test cell, and observing a phenotype of the test cell upon expression of the siRNA encoded by the DMSG cassette, whereby a comparison of the phenotype of the test cell as compared to a control cell is indicative of a function of the target gene, thereby assessing the function of the gene in the test cell. A test cell can be any cell in which it is desired to express siRNA to determine how RNAi mediated by the siRNA effects or affects expression of a gene. A phenotype to be examined generally is a phenotype that is mediated by the target gene, usually by an RNA encoded by the gene, and particularly by a polypeptide encoded by the gene. As such, it will be recognized that the phenotype to be examined will depend on the particular target gene. In one embodiment, the method provides a means to identify a phenotype conferred by a target gene.

The invention also provides a method for determining whether an agent effects or affects a specific gene in a test cell. The terms "affect" and "effect" are used herein to refer to the causal action by an agent ("effect") and the results of such an action ("affect"). Although reference generally is made herein to an "effect" due to an agent, it will be recognized that an agent identified as an "effector" agent affects expression of a target gene. A method of determining whether an agent effects a specific gene in a cell can be performed, for example, by expressing an siRNA including the intermediate siRNA encoded by at least one DMSG cassette of the invention in the test cell, wherein the intermediate siRNA comprises a 5' portion complementary to an RNA molecule encoded by the specific gene in the test cell, contacting the test cell and a control cell with the agent, and comparing a phenotype of the test cell with that of the control cell, thereby assessing whether the agent effects the specific gene in the test cell. In one embodiment, the method includes expressing a first intermediate siRNA encoded by a first DMSG cassette and a second intermediate siRNA encoded by a second DMSG cassette in the cell, wherein the first intermediate siRNA comprises a 5' portion complementary to a sense strand of a target RNA, wherein the second intermediate siRNA comprises a 5' portion complementary to an antisense strand of the target RNA, and wherein the 5' portion of the first intermediate siRNA is complementary to the 5' portion of the second intermediate siRNA. A change in the phenotype of the test cell as compared to the phenotype of the control cell identifies the agent as an agent that effects the specific gene.

A screening method of the invention provides the advantage that it can be adapted to high throughput analysis and, therefore, can be used to screen combinatorial libraries of test agents in order to identify those agents that can effect expression of a target gene. Methods for preparing a combinatorial library of molecules that can be tested for a desired activity are well known in the art and include, for example, methods of making a phage display library of peptides, which can be constrained peptides (see, for example, U.S. Pat. Nos. 5,622, 699 and 5,206,347; Scott and Smith, *Science* 249:386-390, 1992; Markland et al., *Gene* 109:13-19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83-92, 1995; a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference); an oligosaccharide library (York et al., *Carb. Res.* 285:99-128, 1996; Liang et al., *Science* 274:1520-1522, 1996; Ding et al., *Adv. Expt. Med. Biol.* 376:261-269, 1995; each of which is incorporated herein by reference); a lipoprotein library (de Kruif et al., *FEBS Lett.* 399:232-236, 1996, which is incorporated herein by reference); a glycoprotein or glycolipid library (Karaoglu et al., *J. Cell Biol.* 130: 567-577, 1995, which is incorporated herein by reference); or a chemical library containing, for example, drugs or other pharmaceutical agents (Gordon et al., *J. Med. Chem.* 37:1385-1401, 1994; Ecker and Crooke, *BioTechnology* 13:351-360, 1995; each of which is incorporated herein by reference). Polynucleotides can be particularly useful as agents that can effect gene expression because nucleic acid molecules having binding specificity for cellular targets, including cellular polypeptides, exist naturally, and because synthetic molecules having such specificity can be readily prepared and identified (see, for example, U.S. Pat. No. 5,750, 342, which is incorporated herein by reference).

The present invention also provides kits, which contain at least one isolated DNA molecule of the invention, at least one DMSG cassette of the invention, or a combination thereof. A kit of the invention also can contain, for example, a reagent useful for introducing such a nucleic acid molecule into a cell, for example, a transfection aid, or can contain one or a selection of different vectors useful for propagating the nucleic acid molecule or for introducing the nucleic acid molecule (e.g., one or more DMSG cassettes) into a particular cell type. Where the kits contains at least one DMSG cassette including a heterologous nucleotide sequence containing a restriction endonuclease recognition site or a recombinase recognition site or a combination thereof, the kit can further include at least one promoter or terminator, or a combination thereof, wherein the promoter or terminator includes a terminus sufficient for operative linkage to the nucleotide sequence encoding the intermediate siRNA. As such, a kit of the invention can contain, for example, a variety of different promoters, enhancers or the like that permit expression of the encoded intermediate siRNA(s) at a desired level in a cell, or in a particular cell type, or under specific conditions such as upon exposure to an inducing agent.

In a still further embodiment, the kit contains a DMSG cassette, wherein the heterologous nucleotide sequence includes at least one promoter, at least one terminator, or a combination thereof. In one embodiment, the heterologous nucleotide sequence comprises a human U6 gene promoter or an RNA polymerase III promoter. In a further embodiment, the heterologous nucleotide sequence comprises at least one enhancer element.

In one embodiment, a kit contains at least two DNA molecules or DMSG cassettes of the invention, wherein intermediate siRNA molecules encoded by two of the nucleic acid molecules can selectively hybridize to form a functional double stranded siRNA molecule. As such, the kit can contain reagents useful for mediating RNAi.

Prior to the present disclosure, RNA mediated gene silencing has been difficult and expensive due to the high cost and low stability of chemically synthesized RNA. The present invention overcomes previous limitations of RNA mediated gene silencing by providing DNA mediated gene silencing, wherein DNA molecules as disclosed herein are used as vehicles to carry the sequence information for RNAi, and as mediators introduced to cells for specific gene silencing. DNA molecules, including dsDNA molecules, provide the additional advantage that they can integrate into the chromosomes of a host cell, thereby generating stable and essentially permanent effects. Such a property allows the generation of transgenic organisms, including plants and animals, that have a permanent RNAi effect, thus providing model systems that allow a study, for example, a function of a gene or combination of genes, and that can mimic a pathologic disorder, particularly a disorder associated with the aberrant lack of function of a gene or gene product. DNA molecules are easier and cheaper to produce and manipulate than RNA. Although modifications on RNA risk loss of its RNAi functions, modifications on DNA, e.g., labeling with a fluorescent marker or conjugation to a polypeptide for targeted delivery at an end or other position that does not alter the function of the DNA molecule, do not change the encoded intermediate RNA molecules or, therefore, the ability to mediate RNAi. Such modifications enable selection of cells that have received the RNAi treatment from those that have not, or targeting a particular type of cells in an organism.

As disclosed herein, DNA molecules, e.g., DMSG cassettes, that encode a sense strand and a corresponding antisense strand of a target RNA molecule mediate gene silencing (see Examples). Generally, the encoded siRNA molecules have a length shorter than about 30 nucleotides, thus minimizing the likelihood that nonspecific repression is activated, and usually have a length of about 20 to 25 nucleotides, particularly about 21 nucleotides, which can effectively induces RNAi (Elbashir et al., *EMBO J*, 23:6877-88, 2001). Also, mismatch between an siRNA strand and a target RNA strand generally is minimized such that selectivity is maximized; usually, there is no mismatch between the two RNAi RNA strands or between the antisense and the target mRNA.

A DMSG cassette containing an enhancer element, a promoter, a template sequence encoding either the sense or the antisense RNA strand, and two transcription terminators is exemplified in FIG. 1A. These elements are designed in accordance with the requirements of the RNA polymerase (pol III in this example) designated for transcribing short RNAs from DMSG cassettes inside target cells. The desired expression level can be achieved by using strong or weak enhancer and promoter elements, multiple enhancer elements, or other elements that can regulate the RNA polymerase activity. In the example depicted in FIG. 1, human RNA polymerase III was selected for transcribing short RNAs from the DMSG cassette, and the human U6 gene promoter was used. An enhancer, the human distal sequence element ("DSE"; ATTGCAT) that stimulates transcription by pol III when naturally located about 224 nucleotides away from the transcription start site of the U6 gene promoter, was positioned in the exemplified DMSG cassette approximately 79 nucleotides upstream of the transcription start site. The DSE is followed downstream in the human U6 gene by a proximal sequence element ("PSE"; CTTACCGTAACT-TGAAAGTA; SEQ ID NO:34; compare mouse PSE; CTCACCCTAACTGTAAAGTA; SEQ ID NO:35, which also can be used in a DMSG cassette) and the TATA box as in a human U6 gene (see, also, SEQ ID NO:36, human U6 gene upstream regulatory sequence, including DSE, PSE, and TATA regulatory elements). An advantage of the U6 gene promoter is that it is entirely outside of the template nucleotide sequence encoding the intermediate siRNA, and an advantage of using a pol III system is that pol III can transcribe approximately 100,000 copies of RNA from only few copies of the gene (Weinberg and Penman, *J. Mol. Biol.* 3:289-304, 1968).

As disclosed herein, an intermediate siRNA can be generated from a DMSG cassette either by including a terminator sequence in the cassette such that the intermediate siRNA is of the appropriate length and contains the desired 3' overhang, or by constructing the DMSG cassette such that the transcript "runs off" of the template. Transcription can be terminated by a "run-off" mechanism, for example, by constructing the DMSG cassette as a linear expression cassette (see FIG. 1B), wherein the cassette ends at the last nucleotide of the template sequence. Similarly, run off can be effected by introducing a restriction endonuclease recognition site at the desired position in the cassette, and cleaving a nucleic acid molecule comprising the DMSG cassette (e.g., a circularized vector containing the cassette) with the appropriate restriction enzyme. In such a way, a transcribing RNA polymerase will run off the template after reaching the end of the template, thus producing the desired intermediate siRNA transcript. Such methods are similar to those used in standard methods of in vitro transcription using, for example, a bacteriophage RNA polymerase such as T7, T3 or Sp6 RNA polymerase or a bacterial RNA polymerase such as an *E. coli* RNA polymerase.

A DMSG cassette containing a terminator element following the template sequence is illustrated in FIG. 1A. The pol III terminator element for the U6 gene is a short sequence that effectively stops transcription at one of the thymine ("T") bases. In conjunction with using this termination element, the RNA sequence for gene silencing can be selected such that the last few bases are uracil ("U"), overlapping with the terminator. In order to prevent a leaky termination event from making long RNAs, a second terminator can be positioned following (downstream of) the first terminator (FIG. 1A). DMSG cassettes containing terminator elements conveniently can be placed in tandem on a linear or circular nucleic acid molecule such as a vector (see FIG. 2).

Nucleotide sequences containing three to five consecutive thymidine residues act as terminators of RNA polymerase III transcription. For example, the human U6 gene RNA polymerase III (pol III) terminator includes the nucleotide sequence TTTTT ACATCA (SEQ ID NO:48), although the end of the terminator has not clearly been defined, and the non-T containing sequence may have an influence on termination. Similarly, the mouse U6 gene pol III terminator includes the nucleotide sequence TTTT gTTcc (SEQ ID NO:49). As discussed above, however, these naturally occurring terminators can be leaky, such that termination does not always end at a specific base. As disclosed herein, modified pol III terminators have been designed to terminate pol III transcription more efficiently, such that a higher percentage of termination events occur within the region of the terminator. In particular, a modified pol III terminator designed from the naturally occurring human U6 gene terminator has the nucleotide sequence TTTTT acag TTTTT g (SEQ ID NO:50; see, also, Example 1, and SEQ ID NO:3) and a modified pol III terminator designed from the naturally occurring mouse U6 terminator has the nucleotide sequence TTTTG TTcg TTTTT g (SEQ ID NO:51; see, also, Example 4, and SEQ ID NO:18).

For broad application, it is desirable that all the elements of the DMSG cassettes be placed on a vector in a manner similar to those used for gene transfer, e.g., transfection and infection. In one embodiment, DMSG cassettes are designed on a vector backbone, which can have one or more of the following characteristics. The vector can have a template cloning site such that a dsDNA oligonucleotide corresponding to the template sequence for a particular target gene routinely can be inserted into the vector without disturbing the overall function of the cassette. The restriction sites can be designed such that, upon digestion, no extra nucleotides are added to or deleted from the promoter and the terminator. Additionally, in the case of using pol III promoter, the first base is a guanine ("G") or an adenine ("A"), which is required by the enzyme as a start nucleotide (Goomer and Kunkel, *Nucleic Acids Res.*, 18:4903-4912, 1992). In one embodiment of the present invention, a Bsm I restriction endonuclease recognition site is used in tandem, and of opposite orientation, between the promoter and the terminator (FIG. 3 and Example 6). In another embodiment, the promoter and/or terminator is flanked by a restriction endonuclease recognition site such that a different promoter/terminator can be inserted in place of the exemplified promoter/terminator. Upon digestion with a restriction enzyme, selected designed sticky ends for inserting template sequence, promoter, terminator, or the like remain intact. Through this design, if guanine and cytosine are selected as the first and the last base of the template sequence, respectively, "extra bases" are avoided and maximum RNAi effects achieved.

Similar design can be achieved with sites for other restriction enzymes. The promoter and terminator can be of any natural or artificial sequence that carries the desired characteristics for transcription with any natural or engineered polymerase. The vector can be any commercially available or specially designed plasmid, virus, phage, phagemid, linear expression vector, or any other type of vehicles that one uses to transfer genetic information.

DMSG cassettes can be delivered by transfection techniques including, but not limited to, calcium precipitation, electroporation, complexation with cationic lipid, complexation with DEAE-dextran, polybrene reagents, or the like. DMSG cassettes also can be introduced into a cell using a mechanical methods such as by microinjection or using biolistic particles. DMSG cassettes carried on viral vectors can be introduced to cells by viral infection. DMSG cassettes can also be delivered by linking the DNA molecules to signal peptides that transduce into cells. For example, DMSG molecules can be conjugated to HIV TAT transduction domain or cell-permeable peptides (Becker-Hapak et al., *Methods* 3:247-256, 2001; Gallouzi and Steitz, *Science* 5548:1895-1901, 2001), which direct the DNA into cells.

DNA molecules can be modified without affecting mediator RNAs for gene silencing. Several applications can be derived from such modifications, including, but not limited to, identifying and selecting cells that have received one or more gene silencing signals, targeting DMSG agents to specific cell populations, delivering other signals or effecter molecules together with DMSG molecules, and the like.

Selection of DMSG-treated cell populations can be achieved by labeling DNA molecules directly with a color marker, such as fluorescein (FITC), R-Phycoerythin, Cy3, Cy5, Texas red, or any other available markers, or with indirect labeling agents such as biotin or digoxigenin, which can be labeled by other color markers via a conjugate. Direct labeling is suitable for following live cells by methods relating to fluorescence-assisted cell sorting (FACS) or fluorescence microscopy. Indirect labeling can require cell or tissue fixation before secondary labeling. In one embodiment, one or both strands of dsDNA that encoded a sense or antisense RNA molecule are labeled with FITC at the 3' end during DNA synthesis. When such DNA molecules are introduced into cells, those that receive the DMSG molecules, and thus are subject to gene silencing effects, can be traced by fluorescence. This enables selection of a specific population of cells, tissues, or an organism for gene functional studies, while artifacts generated by a mixed population of cells can be avoided and thus reliable data obtained. Modification of the DNA molecules can be made at a 3' end, a 5' end, or both, and on either strand of a double stranded nucleic DNA molecule, or can be made on any one or more internal nucleotides using methods as disclosed herein or otherwise known in the art.

The potential for labeling different DMSG cassettes with different markers without affecting their RNA coding capability and the convenience of introducing multiple DMSG cassettes can be used to produce multiple gene knock downs. Genes often function in pathways or networks that involve multiple gene products. Knock down of one gene can reveal only a partial or limited picture of gene function, while knock down of a network of related genes can lead to a more systematic understanding of gene functions and relations. Multiple gene knock downs can also be of practical use for therapy.

DMSG molecules can be used to target specific types of cells. This cell specific targeting can be achieved by conjugating the DMSG molecules to peptides or polypeptides or other targeting modules that direct transduction or endocytosis into a specific cell population.

The ease and accessibility of DNA molecules for conjugation also make it possible to link DMSG molecules with one or more effecter molecules such as a radioactive isotope, a chemical reagent, a peptide or polypeptide, other polynucleotide molecule or the like that can cause an effect inside a cell. The effects of these molecules co-delivered with DMSG can be achieved and studied in combination with gene silencing in one cell.

The present invention provides methods for studying functions of one or more genes in eukaryotic systems, mammalian cells or organisms in particular. DMSG cassettes targeting a gene(s) of interest are introduced into a cell or organism, i.e., a test cell or test organism. Control DMSG cassettes, buffer, or other mock treatment are applied to a control cell or organism, as appropriate. The test and control cells or organisms are maintained under conditions under which gene silencing takes place. The phenotype of the test cell or organism is observed and compared to that of an appropriate control cell or organism. Such a comparison with the control cell or organism can be made between the aforementioned selected cell populations. For such comparison, control cells are treated with control DMSG cassette(s), which are identical to the non-control DMSG cassette(s) in all respects, including marker labeling, except that the template sequence in the control molecules is not directed against the target gene. The template sequence in the control molecules can be directed against a related or unrelated second gene with the same or different species specificity, or against a non-naturally occurring gene. A difference between the phenotypes of the test and control cells or organisms provides information about the function of the targeted gene. This information can be valuable alone, or can be used in conjunction with information obtained from other assays or analyses to identify or define functions of the gene.

The invention also encompasses methods of determining whether a gene product is a target for drug discovery or development. DMSG cassettes that can induce gene silencing are introduced into a cell or organism. The cell or organism is maintained under conditions under which gene silencing takes place and the targeted cell or organism can be selected by marker(s) carried on the introduced DMSG molecules. Whether decreased expression of the gene has an effect on the cell or organism is determined, wherein if decreased expression of the gene has an effect then the gene product is a target for drug discovery or development. The effect can be cell death, differentiation, cell division variation, or any other cellular reactions. The target gene can be, among others, any natural gene of cellular origin, such as genes in signal transduction or cell cycle control, or of viral or other pathogenic origin, such as genes involved in life cycles of hepatitis, HIV, or other viruses.

Also provided are methods for producing genetically modified organisms, wherein one or more DMSG cassettes is inherited from one generation to the next through duplication of chromosomes. In one embodiment, DMSG molecules against any particular gene or genes can be introduced by microinjection into an early-stage embryo and become part of its chromosome. Animals derived from the germ cells with integrated DMSG molecules can pass the transgenic DMSG DNA as an integral part(s) of its chromosome to the following generations, thereby creating animals with the target gene(s) interfered by the intermediate RNAs encoded by the DNA insert. Compared to current gene knock out methods, DMSG knock down does not rely on homologous recombination and can thus be performed with dramatically higher success rates. Significantly, while multiple gene knockdowns by conventional means is practically very difficult, if not impossible, multiple DMSG gene knockdowns are feasible. DMSG gene knockdown does not necessitate cloning of genomic sequences and manipulating large DNA constructs as traditional gene knockdown methods require. Small DMSG cassettes encoding the sense and the antisense strands of an intermediate dsRNA can be inserted at, in principle, any place along the chromosome for each gene knockdown. Furthermore, as there are chromosomal regions that are inactive or inaccessible to gene transcription (Izumi and Gilbert, *J. Cell Biochem.* 2:280-289, 1999), insulator elements (domain boundaries that can shield sequences between them from regulatory effects of neighboring chromatin domains or elements) can be included in the DMSG cassettes to ensure consistent transcription of the encoded intermediate dsRNA molecules.

A DMSG cassette can be microinjected into pronuclear embryos. Some cells of the injected embryo that have integrated DMSG molecules will develop into germ-line cells. Second generation animals derived from these germ-line cells will carry DMSG cassettes as segments of their chromosomes. Other animals such as a fly, worm, or zebrafish with integrated DMSG molecules can also be produced with appropriate transgenic methods, as can plants.

The present invention also provides methods for controlling gene knock down. The time and level of gene knock down can be manipulated by controlling the transcription of the DMSG DNA. In one embodiment, DMSG cassettes are made under the control of an exogenous RNA polymerase, such as a transgenic T7, T3, Sp6, or *E. coli* RNA polymerase. The gene encoding the polymerase is in turn controlled by an inducible promoter, e.g., a promoter that is only transcribed by endogenous pol II in the presence of an inducing agent (inducer) such as tetracycline or ecdysone. In practice, when the gene knockdown is desired at a specific time point such as a developmental stage, the inducer is added so that the exogenous RNA polymerase is expressed, which subsequently transcribes the intermediate RNAs encoded by the DMSG cassettes. In another embodiment, the exogenous RNA polymerase is under the control of a tissue-specific promoter, and therefore, only expressed in a particular tissue or organ, e.g., exocrine pancreas, heart myoblasts or neuronal cells. In consequence, DMSG gene silencing is only activated in that particular tissue or organ. This method can be used in combination with inducible and multiple DMSG gene knockdowns.

The present invention also provides compositions and methods for therapy or preventive treatment for diseases. DMSG molecules can be introduced into an organism to silence a target gene, thereby reverting or preventing an abnormality or disease. DMSG molecules, alone or in therapeutic compositions such as appropriate buffer and additional reagents, can be delivered through direct application to the surface of an organism or to the cells under the surface by means such as a gene gun. The delivery can also be internal administration, e.g., by injection or delivered orally in appropriate compositions such that the integrity of the DNA molecules is protected and the effects of gene silencing are produced. The DMSG molecule treatment can be permanent through the germ line if the DNA molecules are integrated into the host chromosome.

Identifying genes with a known function is traditionally carried out by genetic screening, or by isolating the gene product through biochemical procedures. However, such identifications can also be done by "molecular evolution", i.e., enriching and selecting the desired genetic information from a pool of DNA or RNA molecules, or by reverse genetics, i.e., altering all or a group of genes and detecting which one(s) carries the function under study. An example is the SELEX (systematic evolution of ligands by exponential enrichment) procedure for selecting high-affinity ligands to a target protein from a pool of variant RNA or DNA sequences (Gold, Harvey Lect, 47-57, 1995; Wang et al., *J. Biol. Chem.* 35:22227-22235, 1997; White et al., *J. Clin. Invest.* 8:929-934, 2000). This concept is also demonstrated by examples such as phage display and ribosome display for selecting proteins with desired binding abilities from a random or preferred pool (Crameri and Kodzius, *Comb. Chem. High Throughput Screen* 2:145-155a, 2001; Schaffitzel et al., *J. Immunol. Methods* 1-2:119-125, 1999). The gene silencing signal on a DMSG cassette is in the form of short template sequences and, therefore, suitable for being varied as a degenerate pool from which selection can be performed. To generate a random DMSG cassette pool, chemically synthesized single stranded DNA oligonucleotides with degenerate template sequences are converted into dsDNA by DNA polymerase (e.g., T7 DNA polymerase; a T7 polymerase promoter is exemplified by 5'-TAATACGACTCACTAT-3' (SEQ ID NO:37). The dsDNA template sequences are either ligated to a DMSG cassette where both DNA strands can be used for transcription, or cloned in opposite orientation into each cassette on a double-cassette DMSG molecule. The dsDNA nature of DMSG cassettes as opposed to dsRNA of RNA-mediated RNAi facilitates molecular cloning of any selected sequences. Consequently, protocols relating to the design and use of DMSG cassettes can be practically applied to identify genes which, when knocked down, can change a cellular event(s) and thereby produce a specific phenotype(s), such as, among others, arrest of cell cycle, apoptosis, cell differentiation, cancerous transformation, and response or resistance to drug treatment.

The present invention thus relates to methods of identifying genes with specific functions and when knocked down, demonstrate specific phenotypes. In one embodiment, each base of the template nucleotide sequence is a random choice of the 4 natural bases, namely, A, C, G, or T, thereby generating a pool of DMSG cassettes with potential to match any gene in a cell. The DNA molecules, which are identical in all the regions except the template region (randomized during DNA oligonucleotide synthesis), are then transfected into a sufficient number of cells. One or multiple steps of cell selection can be performed to isolate the cells that show the phenotype being sought after. Double stranded DNA molecules can be retrieved from these cells and either amplified for further rounds of enrichment and selection or cloned and sequenced. From template sequences on the isolated DMSG cassettes candidate genes with functions of interest can be identified. Such genes are then cloned by molecular biology methods or identified using bioinformatics methods.

The present invention also provides methods for isolating RNA molecules with specific functions. Similar to the gene identification method described above, DMSG cassettes encoding a pool or a combination of candidate RNAs can be introduced into a population of cells or organisms from which those with the phenotype under study are selected. The functional RNA sequences are obtained by cloning the dsDNA and sequencing the template regions. Functional RNAs that can be selected this way include, but not limited to, siRNA molecules with high efficiency and specificity, RNAs other than siRNA molecules (such as those with hairpin structures) that can have RNAi effects, antisense RNAs, and RNA components of functional complexes such as chromosome inactivation complex (Meller et al., *Cell* 4:445-457, 1997).

The invention further relates to methods of studying the biological functions of non-coding RNAs in a eukaryotic cell. It has been reported that in many animals there exist natural small RNA (microRNA; miRNA) molecules that are processed through a pathway related to RNAi (Grishok et al., *Cell* 1:23-34, 2001; Hutvagner et al., *Science* 5531:834-838, 2001; Ketting et al., *Genes Devel.* 20:2654-2659, 2001; Lagos-Quintana et al., *Science* 5543:853-858, 2001; Lau et al., *Science* 5543:858-862, 2001; Lee and Ambros, *Science* 5543:862-864, 2001). DMSG cassettes encoding such RNAs (or their antisense strands or variants) can be used in a transfected cell to study the functions of these RNAs. In this respect, it should be recognized that, like any RNA, miRNA can be target for siRNA. In addition, miRNA and siRNA are similar in that each is a short RNA molecule that lacks a poly(A) tail and is recognized by factors involved in the RNAi process. Because DMSG cassettes are designed to transcribe short, defined RNA, the framework of such cassettes, including, for example, a template cloning site operatively linked to an enhancer, promoter, terminators, or combination thereof, are suitable for expressing miRNAs by replacing siRNA template with miRNA template.

DNA mediated RNAi is used to knock down gene-specific expression in human and other eukaryotic cells. As disclosed herein, gene silencing is achieved more efficiently by the DNA mediators than the corresponding RNA mediators, i.e., siRNA, on an equal molar basis, due, perhaps, to a continuous production of intermediate siRNA molecules of both the sense and the antisense sequence of the target gene, such that a functional double stranded siRNA can form inside the cell and activate RNAi against a specific gene. Accordingly, the present invention relates to DNA molecules that contain the genetic information for specific gene suppression. DNA molecules containing a template sequence corresponding to a target gene can mediate gene suppression through RNAi. While the DNA molecules of the invention are exemplified using naturally occurring nucleotides, it will be recognized that nucleotide analogs, including non-naturally occurring synthetic nucleotides or modified naturally occurring nucleotides, also can be used to construct the nucleic acid molecule, e.g., a DMSG cassette. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference). Similarly, while the covalent bond linking the nucleotides of a polynucleotide generally is a phosphodiester bond, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994); Ecker and Crooke, *BioTechnology* 13:351-360, 1995, each of which is incorporated herein by reference). The incorporation of non-naturally occurring nucleotide analogs or bonds linking the nucleotides or analogs can be particularly useful where the DMSG cassette is to be exposed to an environment that can contain a nucleolytic activity, including, for example, a tissue culture medium or upon administration to a living subject, since the modified nucleic acid molecules can be less susceptible to degradation.

A template nucleotide sequence is an element of an isolated DNA molecule (or DMSG cassette) of the invention corresponding to at least a portion of the sequence of a target gene. As such, the template encodes the intermediate siRNA molecules that form an siRNA and trigger RNA degradation by the cellular RNAi machinery complex. Target mRNA and target RNA herein refer to the RNA that is to be prohibited from functioning with the introduction of DMSG molecules. Such RNA can be transcribed from endogenous or exogenous genes, or introduced as RNA by transfection or other means of transferring from outside to inside a cell or organism, and can, but need not, encode a polypeptide. An intermediate siRNA, which is transcribed from a DMSG cassette, can form, in part or in whole, a guide RNA, which can base pair with a target RNA and direct target RNA degradation.

The present invention relates to DNA molecules containing a designed template sequence that can be transcribed into RNAs of shorter than 30 nucleotides. One major concern of using DNA mediated gene-specific silencing is to control the expressed RNAs (sense and antisense) within limited length, e.g., shorter than 30 nucleotides, so that interferon- and PKR-mediated global shutdown of the host cells is not induced under the conditions for RNAi. Of the mammalian RNA polymerases, pol III stops RNA elongation by transcriptional termination. In one embodiment of the present invention, naturally derived or modified pol III termination sites are used in the DMSG cassette to achieve RNA length limits. This mechanism can be used in either a linear or a circular format of the cassette. In another embodiment, the DMSG cassette was designed in a linear format that the template sequence is followed by no other sequences. As a result, the transcribing RNA polymerase inside the target cell will "run-off" the template and make short RNAs. The transcribing RNA polymerase for such run-off DMSG cassette can be any of the endogenous or exogenously introduced RNA polymerase.

The present invention also relates to DMSG cassettes that encode either the sense or antisense sequence of a region of the target gene. To transcribe a template sequence into RNA at levels and in forms suitable for inducing RNAi in mammalian cells, such DMSG cassette can include an enhancer(s) for a particular RNA polymerase, including, but not limited to, RNA polymerase I, II, and III of mammalian cells. The cassette can also contain a promoter for the RNA polymerase intended for transcribing the template sequence. The enhancer helps drive the transcription of the template sequence from the promoter. The enhancer and the promoter, followed by the template sequence, can be either arranged in a linear order as stand-alone cassette or carried on a circular vector such as a plasmid or virus or other vectors that can be propagated.

The present invention relates to DMSG cassettes containing all essential DMSG elements in a linear format. In one embodiment, each intermediate RNA strand, sense or antisense, is encoded by a dsDNA encompassing a preferred DMSG cassette. The cassette contains minimum elements of a promoter, a template sequence, followed by a terminator or an abrupt end. The DMSG cassette can contain enhancer(s) that helps produce a desired level of transcripts in target cells. In this embodiment, the dsDNA is annealed from two synthetic DNA strands produced as one continuous molecule using a chemical synthesis method.

The invention also relates to DMSG cassettes in a linear format encoding the sense or the antisense intermediate RNA, not a continuous DNA strand. In one embodiment, a linear cassette is assembled by annealing synthetic DNA oligonucleotides, each of which is part of either one of the two strands of the DMSG dsDNA. Such dsDNA of DMSG can be produced by other methods, which include, but are not limited to, ligation (with ligase) of such oligonucleotides or amplification with molecular biology methods such as polymerase chain reaction ("PCR") that results in a continuous dsDNA molecule. Such DNA molecules can also be produced by molecular cloning or recombinant techniques, including processing or cleaving DNA fragments, which by themselves do not mediate RNAi if transfected into a cell or organism.

Further, the invention relates to DMSG cassettes in a linear format encoding both sense and antisense intermediate RNAs. Such dsDNA can be described as having two sets of cassettes on one assembly of dsDNA (with or without nicks), each one encoding either the sense or the antisense intermediate RNA. Such "double cassette" DNA can be annealed from chemically (or recombinantly) synthesized long DNA oligonucleotides or from shorter oligonucleotides that are subsequently assembled and ligated, and can be amplified by PCR.

The invention also relates to DMSG cassettes that are carried on a vector, which can be a plasmid, phage, virus, or any other type of vectors that can be used to carry genetic information into a target cell, or on any common or specially designed DNA construct that can carry an inserted piece of DNA. This can be done by inserting the said cassette into the vector by molecular methods, including, but not limited to, ligation and recombination. Accordingly, the invention also relates to modified vectors and methods of modifying a vector, wherein a template sequence, which encodes either the sense or antisense siRNA sequence, can be inserted. This can be achieved by first inserting the DMSG elements described above, i.e., the enhancer and the promoter, into a vector, which is followed by a template cloning site, where restriction enzyme sites can be used to linearize the vector for insertion of the template sequence. The template cloning sequence is followed by a terminator region. In particular, as described herein, the sites are so chosen and designed that the template sequence inserted into the site is to be transcribed in a target cell without any nucleotide(s), or with limited number of nucleotide(s), that are not encoded by the template sequence. Nucleotide(s) not encoded by the template sequence are not desired, as they can diminish or destroy specific RNAi effects (Elbashir et al., *EMBO J.* 23:6877-6888, 2001; Parrish et al., *Mol. Cell* 5:1077-1087, 2000).

The present invention also relates to methods of mediating RNA interference of a gene in a cell or organism or tissue(s), including, for example, heart, lung, colon, kidney, or skin, of an organism. In one embodiment, DMSG cassettes, which have the ability of directing transcription of sense and antisense RNAs that can trigger degradation of target mRNA, are introduced into a cell or organism. The cell or organism is maintained under conditions under which degradation of the target mRNA takes place, thereby mediating RNAi in the cell or organism.

The present invention also relates to methods of knocking down, either partially or completely, a target gene, providing an alternative method for gene knock out or previous methods of gene knock down using RNA molecules. The term knock down or knock out is also used to refer to the effect on a cell or organism of which gene function is eliminated (inhibited) or diminished (reduced) as compared to a corresponding normal (i.e., unmodified) cell or organism. The present invention also relates to methods of producing knock down cells or organisms that comprise introducing into a cell or organism, in which a target gene is to be knocked down, DMSG cassettes that encode RNAs that target the gene, maintaining the cell or organism under conditions under which gene silencing take occurs, and producing knockdown or knockout cells or organisms.

The invention also relates to methods of tracking, among a population of cells, a specific group of cells that are subject to DMSG treatment. In one embodiment, one or both strands of dsDNA encoding sense or antisense RNA is labeled with a marker. When such DNA molecules are introduced into cells, those that receive the DMSG, and are thus subject to gene silencing effects, can be traced through the marker. This method enables the selection of a specific population of cells or part(s) of tissues or an organism, where artifacts generated by mixed population of cells can be avoided. The cell population or tissue collection selected by this method where gene silencing effects can be followed is also the subject of this invention.

The invention further relates to methods of studying gene silencing effects of further selected cell populations where more than one gene are targeted with separate DMSG cassettes, of which the DNA molecules can be labeled with distinguishable markers. The selected cell population or tissues or organisms, in which multiple genes are knocked out, are also the subject of this invention.

In addition, the invention relates to methods of examining or assessing the function of a gene in a cell or organism with DMSG cassettes. In one embodiment, DMSG cassettes, which comprise a specific template sequence and induce gene silencing, are introduced into a cell or organism. The cell or organism is referred to as a test cell or organism. The test cell or organism is maintained under conditions under which gene silencing takes place. The phenotype of the test cell or organism is then observed and compared to that of an appropriate control cell or organism, which is not targeted with the same DMSG cassettes. A difference between the phenotypes of the test and control cells or organisms provides information about the function of the targeted gene.

The invention also relates to methods for determining whether an agent has any effect on a specific gene. In this method, DMSG cassettes that induce gene silencing are introduced into a cell or organism. The cell or organism is maintained under conditions under which gene silencing takes place and the targeted cell or organism is selected by marker(s) carried on the introduced DNA molecules. A test agent, which can be any molecule or composition, including, but not limited to, a peptide, protein, chemical reagent or composition, gene therapy vehicle or composition, is introduced into the test cell or organism, to control cell or organism where gene silencing does not take place. Phenotypes of the test cell or organism and the control cell or organism after the agent treatment are used to determine the functional relations between the agent and the target gene.

The invention also relates to methods of identifying RNA molecules with a specific function from a pool of random sequences. High recovery rate is critical for any selection procedure from a degenerate pool. However, direct cloning of short RNAs such as siRNA requires multiple difficult steps including RNA isolation and ligation to adapters, and reverse transcription PCR, which, together, can result in low recovery rate. The dsDNA nature of DMSG cassettes facilitate efficient recovery of sequences of short RNA molecules after selection. RNA molecules with specific functions that can be selected include, but are not limited to, siRNA molecules, RNA molecules other than siRNA molecules such as those with hairpin structures that can have RNAi effects, antisense RNA molecules, RNA components of functional complexes such as chromosome inactivation complex. Also encompassed by the present invention is a method of identifying regions within a target RNA that are particularly suitable for DMSG, as well as a method of assessing the ability of any sequence carried on DMSG cassette to mediate gene silencing. Accordingly, the invention also provides DMSG cassettes identified using such a method.

The present invention also relates to methods of using DNA molecules or compositions comprising such DNA molecules for research as well as therapeutic or prophylactic treatment, for example, to generate research models of disease states, to search for targets for drug discovery and development, or to treat a disease or condition associated with the presence of a protein or non-coding functional RNA. These include, but are not limited to, using DMSG cassettes, compositions containing DMSG cassettes, kits for administrating such cassettes, and pharmaceutical compositions comprising such cassettes and appropriate carriers for research or therapeutic purposes.

The present invention further relates to methods of inducing gene silencing in a specific cell population or tissue type by specifically delivering DMSG cassettes into the selected target cells. The dsDNA can be conjugated with signal molecules such as a peptide or polypeptide (e.g. cytokine), an antibody, or a chemical group(s) that has specific affinity to a protein expressed on the surface of only the target cells. The cell surface protein can be a receptor, an extracellular matrix binding protein, or other cell surface molecules. Upon binding to the surface molecules, the signal molecules, through endocytosis or other mechanisms, are transferred inside the target cells. The conjugated DMSG dsDNA molecules are internalized together with the signal molecules. Other cells that do not express the specific surface molecules are not subject to gene silencing effects mediated by DMSG. Once inside the target cell, the DMSG cassettes express the intermediate RNAs that can induce gene silencing. Such methods have potential use in both research and therapy. Also encompassed within the invention is a gene identified by sequencing of a template sequence on a DMSG cassette that, when introduced into cells, produces a specific phenotype. In addition, the present invention provides a method to map the networking relationships of cellular or tissue functions of various genes.

The following examples are intended to illustrate but not limit the invention.

EXAMPLES

RNAi has become a popular technique in functional genomics because of its efficiency and specificity in knocking down the expression of the targeted gene. The current methods include either dsRNA or siRNA (21-23 nucleotides, small interfering RNA) mediated gene silencing, and long dsRNA molecules appear to be more efficient. However, in higher animals, the RNAi mediated gene silencing can only be achieved with short dsRNA molecules due to the activation of PKR and interferon responses by long dsRNA. The system disclosed herein utilizes continuous transcription of both strands of a region of a target gene in living cells by specifically designed DNA cassettes.

The effectiveness of the present invention is demonstrated in Example 1 using a version of the green fluorescent protein ("GFP") as the target gene; specificity of the compositions and methods is demonstrated in Example 2. Example 3 demonstrate the feasibility of combining the DMSG technology with assembled expression cassettes. Because long oligonucleotides (e.g., >80 nucleotides) are difficult to synthesize, this variation makes generating the cassettes more practical. Example 4 illustrates a modified DMSG cassette using lacZ as the target gene in a mouse cell line. Example 5 and 6 demonstrate that DMSG cassettes can be carried on a conventional circular vector.

Example 1

Targeted mRNA Degradation by Linear DMSG Cassettes

Oligonucleotides for DMSG cassettes specific for a nucleotide sequence encoding green fluorescent protein (GFP) were synthesized at the Core Facility of Allele Biotechnology & Pharmaceuticals, Inc. (San Diego Calif.). In general, the expression cassette (from 5' to 3') consists of an enhancer region, the distal sequence element (DSE, −79 to −72 in reference to the transcription start site on the cassette) for pol III gene U6 (human), a proximal sequence element (PSE, −66 to 47) for pol III human gene U6, a TATA box (−31 to −26), followed by the template sequence (21 nucleotides), a terminator of the U6 gene, and an artificial terminator ("TM" or "Term"). For RO cassette, the terminators were omitted. A single expression cassette is composed of two DNA strands (sense strand and antisense strand) annealed together. The annealing was performed by incubating the two DNA strands in the annealing buffer (50 mM NaCl and 50 mM Tris-HCl, pH7.4) for 1 min at 90° C., then for 15 min at room temperature.

DMSG cassettes expressing the sense or antisense transcript were designated as (+) or (−), respectively. For convenience of subsequent cloning, sticky ends of restriction sites for Bgl II and Nhe I were added to the 5' and 3' of the "TM" cassettes (122 bp), respectively, and 5' end (Bgl II) of the RO cassettes (109 bp). For the TM DMSG(+) cassettes, the sense strand of the dsDNA encoding the sense RNA of a partial sequence of the GFP gene, hP3GFP(+)TMs, is annealed with the antisense strand of the dsDNA encoding the same sense RNA, hP3GFP(+)TMas. The two DNA strands encoding the antisense RNA of the GFP target sequence are annealed to produce the TM DMSG(−). The two TM DMSG cassettes are used together to induce gene silencing. Similarly, the RO DMSG(+) and (−) cassettes are generated with respective DNA strands (hP3GFP(+)s annealed with hP3GFP(+)as and hP3GFP(−)s annealed with hP3GFP(−)as) and used to knock down GFP expression.

The following oligonucleotides were used:

```
hP3GFP(+)ROs:
5'-gatcTATTTGCATggactatcatatgcttaccgtaacttgaaagtatttcgatttcttggctttatatatcttgtggaaaggacgaaaca
ccGAACGGCATCAAGGTGAACTT-3' (SEQ ID NO:1; 113 nucleotides)

hP3GFP(+)ROas:
5'-AAGTTCACCTTGATGCCGTTCggtgtttcgtccttTccacaagatatataaagccaagaaatcgaaatactttcaagtta
cggtaagcatatgatagtccATGCAAATA-3' (SEQ ID NO:2; 109 nucleotides)

hP3GFP(+)TMs:
5'-gatcTATTTGCATggactatcatatgcttaccgtaacttgaaagtatttcgatttcttggctttatatatcttgtggaaaggacgaaaca
ccGAACGGCATCAAGGTGAACTTttt acaGTTTTTg-3' (SEQ ID NO:3; 126 nucleotides)
```

```
hP3GFP(+)TMas:
5'-CTAGcAAAAACtgtaaaAAGTTCACCTTGATGCCGTTCggtgtttcgtcctttccacaagatatataaagcca
agaaatcgaaatactttcaagttacggtaagcatatgatagtccATGCAAATA-3' (SEQ ID NO:4; 126 nucleotides)

hP3GFP(-)ROs: 5'
5'-gatcTATTTGCATggactatcatatgcttaccgtaacttgaaagtatttcgatttcttggctttatatatcttgtggaaaggacgaaaca
ccGTTCACCTTGATGCCGTTCTT-3' (SEQ ID NO:5; 113 nucleotides)

hP3GFP(-)ROas:
5'-AAGAACGGCATCAAGGTGAACggtgtttcgtcctttccacaagatatataaagccaagaaatcgaaatactttcaagtt
acggtaagcatatgatagtccATGCAAATA-3' (SEQ ID NO:6; 109 nucleotides)

hP3GFP(-)TMs: 5'
5'-gatcTATTTGCATggactatcatatgcttaccgtaacttgaaagtatttcgatttcttggctttatatatcttgtggaaaggacgaaaca
ccGTTCACCTTGATGCCGTTCTTtttacaGTTTTTg-3' (SEQ ID NO:7; 126 nucleotides)

hP3GFP(-)TMas:
5'-CTAGcAAAAACtgtaaaAAGAACGGCATCAAGGTGAACggtgtttcgtcctttccacaagatatataaagc
caagaaatcgaaatactttcaagttacggtaagcatatgatagtccATGCAAATA-3' (SEQ ID NO:8)
```

Cell Culture and Transfection:

293T (human embryonic kidney) cells were grown in Dulbecco's modified Eagle's medium (Life Technologies, Rockville, Md.) supplemented with 10% FBS, 100 units/ml penicillin, and 100 μg/ml of streptomycin in a 37° C. $CO_2$ incubator. Cells were regularly passed to maintain growth. Twenty-four hours before transfection, cells were trypsinized and plated on 24-well plates (500 μl/well) in the above medium without the antibiotics. 70-80% confluent cells were transfected with LIPOFECTIN 2000 transfection reagent according to manufacturer's protocol with minor modifications (Invitrogen, Carlsbad): for each transfection reaction, 2 μl of LIPOFECTAMINE 2000 transfection reagent was mixed with 50 μl of serum-free, antibiotic-free DMEM, and incubated for 5 min at room temperature. DMSG DNA or siRNA along with the GFP encoding plasmid were also mixed with 50 μl of serum-free, antibiotic-free DMEM. The diluted LIPOFECTAMINE 2000 transfection reagent was then added dropwise to the diluted DNA or RNA, and incubated at room temperature for 20 min before added to cells. One μg of pEGFP Vector plasmid (CLONTECH) was used for each well. Transfection efficiency was monitored by fluorescence microscopy. Different concentrations (3 pmole or 45 pmole) of linear expression cassettes ("RO" or "TM") were used in co-transfections with the pEGFP plasmid. GFP siRNA was used as positive control. Transfections with no plasmid or transfection reagent were also included as controls of the experiment. Forty-eight hours after transfection, the cells were analyzed under an inverted fluorescence microscope (Zeiss).

To evaluate whether the transcripts generated from the DMSG cassettes against GFP expression could specifically block gene expression, pEGFP plasmid was used as a reporter in a co-transfection study. GFP expression was reduced in cells transfected with GFP siRNA. Importantly, a comparable level of GFP down-regulation in cells transfected with 3 pmole of both (+) and (−) DMSG cassettes was also observed. Moreover, cells transfected with 45 pmole of both cassettes were completely negative for GFP expression. The expression of GFP in these cells was monitored for over 2 weeks and the gene silencing effects by DMSG was persistent during this time period. Only after 20 days did some of the cells transfected with pEGFP and both cassettes appeared to show green fluorescence, presumably from the co-transfected pEGFP plasmids that lasted through cell divisions. This is likely due to the fact that linear dsDNAs are more prone to degradation than plasmid DNA, indicating that the silencing of GFP expression is at the mRNA level as opposed to other effects such as rearrangement or loss of the pEGFP plasmid.

Gene silencing effect through siRNA was lower compared to that of DMSG cassettes, although the amount of GFP siRNA in molar amount was about 10 fold higher than that of the low concentration DMSG cassettes used (i.e. 3 pmole). These observations indicate that linear DMSG cassettes are more effective and can produce more profound gene silencing results than siRNA, probably due to the continuous generation of mediating dsRNAs by the DMSG cassettes. It is noted that DMSG cassettes encoding either the plus or the minus strand of dsRNA corresponding to the GFP gene slightly reduced the expression of GFP, possibly due to unknown "co-repression" effects observed in other species such as fungi (Cogoni and Macino, *Nature* 6732:166-169, 1999), or antisense effects in the case of the minus strand cassette. It was also observed that co-transfection with unrelated DNA or RNA delayed the expression of the target gene, possibly by interfering with certain step(s) during transfection and ectopic expression (data not shown). This can also contribute to the lowered expression by (+) or (−) cassette alone at the time of the observation. Results of this example show that dsDNAs can mediating gene silencing in eukaryotic cells.

Example 2

Mismatches on the Antisense Strand of the DMSG Cassette Affect Gene Silencing

The dsDNA encoding the sense RNA strand was the same as in Example 1 (SEQ ID NO:3 and SEQ ID NO:4). The sense strand of the dsDNA encoding the antisense RNA was also the same as in Example 1 (SEQ ID NO:7), whereas the antisense strand of the dsDNA contained mismatches compared to the GFP sequence. The TM DMSG(+) cassette encoding the sense RNA of a partial sequence of GFP was produced by annealing DNA oligonucleotides hP3GFPTM(+)s and hP3GFPTM(+)as as in Example 1. The DMSG(−) cassettes encoding the antisense RNA of the target sequence of GFP with various mutations were generated by annealing the hP3GFPTM(−)s with hP3GFPTM(−)asM1, M2, M3, or M4, respectively. The transfections were done as in Example 1.

The oligonucleotides, in which mismatched bases are in bold and italicized, were as follows:

```
hP3GFPTMasM1:
5'-CTAGcAAAAACtgtaaaAAGAACGGCATgAAGGTGAACggtgtttcgtcctttccacaagatatataaagcc
aagaaatcgaaatactttcaagttacggtaagcatatgatagtccATGCAAATA-3' (SEQ ID NO:9; 126
nucleotides);

hP3GFPTMasM2:
5'-CTAGcAAAAACtgtaaaAAGAACGGgATgAAGGTGAACggtgtttcgtcctttccacaagatatataaagcc
aagaaatcgaaatactttcaagttacggtaagcatatgatagtccATGCAAATA-3' (SEQ ID NO:10; 126
nucleotides);

hP3GFPTMasM3:
5'-CTAGcAAAAACtgtaaatAGAACGGCATCAAGGTGAAgggtgtttcgtcctttccacaagatatataaagcca
agaaatcgaaatactttcaagttacggtaagcatatgatagtccATGCAAATA-3' (SEQ ID NO:11; 126
nucleotides)

hP3GFPTMasM4:
5'-CTAGcAAAAACtgtaaaAAGAACGGCATCAAGGTGAtgggtgtttcgtcctttccacaagatatataaagcca
agaaatcgaaatactttcaagttacggtaagcatatgatagtccATGCAAATA-3' (SEQ ID NO:12; 126
nucleotides)
```

To evaluate the mechanism and specificity of DMSG, single or double point mutations were introduced into the template sequence region at different positions on the antisense strand of a linear DMSG cassette. A close correlation between the degree of gene silencing and the number of mutations was observed. Also, mutations around the center of the template sequence might have stronger effects on gene silencing than those near the ends. These results indicate that the target recognition process is sequence-specific and not all positions on a template sequence contribute equally to target recognition.

Example 3

DMSG Cassettes Assembled from Short Oligonucleotides Mediate Gene Silencing

Experimental methods are as in the previous examples, except that the dsDNA was assembled from shorter oligonucleotides (FIG. 3). DMSG cassettes can be more easily prepared from shorter oligonucleotides than a continuous long sequence. Assembling DMSG cassettes from short oligonucleotides has practical implications in that, for each gene silencing, one can only need to synthesize a pair of short oligonucleotides corresponding to a template sequence, which can then be assembled with other common oligonucleotides of other components of DMSG cassettes.

Short oligonucleotides, hP3GFPTM(−)s1, s2, s3, as1, and as2, were used to assemble the TM DMSG(−) cassette targeting GFP. Equal molars of these oligonucleotides were mixed and annealed as in Example 1, and then used for co-transfection with pEGFP and the TM DMSG(+) cassette targeting GFP. Transfection and cell cultural methods are the same as in Example 1.

The oligonucleotides were as follows:

DMSG cassettes assembled from these short oligonucleotides produced gene silencing results at a level similar to that produced by a synthesized continuous cassette of Example 1. The result of this example indicates that discontinuous oligonucleotides, when designed appropriately, can be used as transcription template for gene silencing.

Example 4

Labeled DMSG Cassettes Cause Gene Silencing in Mouse Cells and in Human Cells

Murine U6 gene elements equivalent to those used in the hp3GFPTm DMSG cassettes of Example 1 were designed on either continuous or assembled cassettes targeting the lacZ gene. DNA oligonucleotides were annealed and either transfected into an NIH3T3 cell line that stably expresses the lacZ gene or co-transfected with a lacZ reporter plasmid, pCMVβ (Clonetech), into 293T cells. DSE, PSE, TATA box and the terminators are highly conserved between the mouse and human U6 genes.

Forty eight to 72 hr after transfection, cells were washed with PBS, fixed with 1% glutaraldehyde solution (in PBS) for 15 min at room temperature. The cells were then washed twice with 1 mM $MgCl_2$ in PBS before adding X-GAL staining solution (1 mg/ml in N,N-dimethylformamide, 5 mM $K_3Fe(CN)_6$, 5 mM $K_4Fe(CN)_6 \cdot 3H_2O$, 1 mM $MgCl_2$ in PBS, 0.3 ml/well of a 24-well plate). The reaction mixtures were incubated with fixed cells at 37° C. for 10 min to 3 hr until the color develops to a desired level. The cells were washed 3 times with water and stored in dark at 4° C. Cells on cover

```
hP3GFPTM(-)s1:   5'gatcTATTTGCATggactatcatatgcttaccgtaacttgaa 3' (SEQ ID NO:13);

hP3GFPTM(-)s2:   5'agtatttcgatttcttggctttatatatcttgtggaaaggacga 3' (SEQ ID NO:14);

hP3GFPTM(-)s3:   5'aacaccGTTCACCTTGATGCCGTTCTTtttacaGTTTTTg 3' (SEQ ID NO:15);

hP3GFPTM(-)as1:  5'CTAGcAAAAACtgtaaaAAGAACGGCATCAAGGTGAACggtgtttcgtcctttccacaagatatat-3'
                 (SEQ ID NO:16);

hP3GFPTM(-)as2:  5'aaagccaagaaatcgaaatactttcaagttacggtaagcatatgatagtccATGCAAATA3' (SEQ ID NO:17).
``` slips were then observed under microscope for blue color. For FITC labeled DNA, cells were also observed under fluorescence microscope.

DNA oligonucleotides mP3LacTM(+)s and mP3LacTM(+)as were annealed as in Example 1 to generate TM DMSG (+) cassette targeting lacZ. DNA oligonucleotides mP3LacTM(−)s and mP3LacTM(−)as were annealed to generate TM DMSG(−) cassette targeting lacZ. In the case of assembled TM DMSG(−) cassettes, mP3LacTM(−)s1 and s2F were annealed with mP3LacTM(−)as, or mP3LacTM(−)as1 and as2F were annealed with mP3LacTM(−)s. "F" indicates that the 3' end of the oligonucleotide was labeled with FITC by using FITC-CPG for DNA synthesis in a standard coupling reaction.

The oligonucleotides were as follows:

```
mP3LacTM(+)s:
5'gatcTATTTGCATacaaaaggaaactcaccctaactgtaaagtaattgtgtgttttgagactataaatatcccttggagaaaagccttgtttGGTAAACAGTTGATTGAACTT ttgttcGTTTTTg-3' (SEQ ID NO:18; 126 nucleotides);

mP3LacTM(-)s:
5'gatcTATTTGCATacaaaaggaaactcaccctaactgtaaagtaattgtgtgttttgagactataaatatcccttggagaaaagccttgtttGTTCAATCAACTGTTTACC TTttgttcGTTTTTg-3' (SEQ ID NO:19; 126 nucleotides);

mP3LacTM(+)as:
5'CTAGcAAAAACgaacaaAAGTTCAATCAACTGTTTACCaaacaaggcttttctccaagggatatttatagtct
caaaacacacaattactttacagttagggtgagtttccttttgtATGCAAATa-3' (SEQ ID NO:20; 126 nucleotides);

mP3LacTM(-)as:
5'CTAGcAAAAACgaacaaAAGGTAAACAGTTGATTGAACaaacaaggcttttctccaagggatatttatagtc
tcaaaacacacaattactttacagttagggtgagtttccttttgtATGCAAATa-3' (SEQ ID NO:21; 126 nucleotides);

mP3LacTM(-)s1:
5'gatTATTTGCATacaaaaggaaactcaccctaactgtaaagtaattgtgtgttttgagacta3' (SEQ ID NO:22);

mP3LacTM(-)s2F:
5'-taaatatcccttggagaaaagccttgtttGTTCAATCAACTGTTTACCTTtgttcGTTTTTt- FITC-3' (SEQ ID NO:23);

mP3LacTM(-)as1:
5'-CTAGcAAAAACgaacaaAAGGTAAACAGTTGATTGAACaaacaaggcttttctccaag ggat-3' (SEQ ID NO:24);

mP3LacTM(-)as2F:
5'-tttatagtctcaaaacacacaattactttacagttagggtgagtttccttttgtATGCAAAt-FITC-3' (SEQ ID NO:25);
``` mP3LacTM(−)s1 and mP3LacTM(−)s2 are two halves of mP3LacTM(−)s; mP3LacTM(−)as1 and mP3LacTM(−)as2 are two halves of mP3LacTM(−)as. "F" following the oligonucleotide name indicates that oligonucleotide is 3' labeled with FITC.

Similar to the experiments where the GFP gene was used as a target in human cells, the mP3DMSG cassettes reduced the cognate lacZ gene expression in mouse cells that were stably transfected with the lacZ reporter gene or in 293T cells that were cotransfected with the reporter gene. FIG. 4 shows the results of co-transfection. Consistent with the observations of Example 1, DMSG cassettes encoding either the plus or the minus strand of dsRNA corresponding to the lacZ gene slightly reduced the expression of the lacZ gene, possibly due to unknown "co-repression" effects observed in other cases such as fungi (Cogoni and Macino, Nature 6732:166-169. 1999), or antisense effects in the case of just the minus strand cassette. Nonetheless, where DMSG cassettes encoding both RNA strands were used, the gene silencing effects were much more profound.

These results show that DMSG DNA molecules labeled with FITC are functional in causing gene silencing. When FITC-labeled DNA oligonucleotides were used to assemble the cassettes, some cells became green-fluorescent which were at the same time not stained blue. This demonstrates that transfection of the DMSG molecules, which resulted in green fluorescence in target cells, induced lacZ gene silencing. DMSG with labeled DNA molecules provides methods for tracking transfected cells to observe gene silencing effects.

Example 5

DMSG Cassettes on a Circular Vector

A DMSG cassette can be carried on a circular vector. The hP3GFPTM(+) cassette with Bgl II and Nhe I overhang is inserted into the Bgl II and Nhe I sites on a pIND/V5-HisA vector (Invitrogen). The hP3GFPTM(−) cassette with Bgl II and Nhe I overhang is inserted into the compatible sites of Bam HI and Xba I restriction enzymes on the same vector. This plasmid, pDMSGGFP(+/−), carries both the hP3GFPTM(+) and hP3GFPTM(−) cassettes and is used for transfection for the purpose of GFP expression silencing. Only one cassette (+ or −) is inserted into the Bgl II and Nhe I sites to create pDMSGGFP(+) or pDMSGGFP(−). If only one cassette (encoding either the (+) or the (−) RNA strand) is inserted into the Bgl II and Nhe I sites, a plasmid containing either cassette is created, which is called pDMSGGFP(+) or pDMSGGFP(−).

In transfection experiments similar to those in Example 1, instead of linear DMSG cassettes, pDMSGGFP(+/−) alone or pDMSGGFP(+) and pDMSGGFP(−) together are used to silence the expression of GFP. The gene silencing effects are expected to last longer than those by linear cassettes as circular dsDNAs are in general more stable than linear cassettes.

Example 6

DMSG Vectors for General Use

This example describes the construction of DMSG vectors that can be used for introducing and expressing various template nucleotide sequences useful for gene silencing effects.

Plasmid pDMSGGFP(+) as described in Example 5 is used to exemplify DMSG vectors. The sequence between the last base of the promoter and the first base of the 5' terminator of plasmid pDMSGGFP(+) is replaced with the nucleotide sequence, CATTCN$_{25}$GAATGC (SEQ. ID. NO:26; only the sense strand is shown, N represents any of the four bases, A, T, C, and G) to generate the vector, pDMSG1 (see, also, SEQ ID NO:44; FIG. 5). To insert a template sequence against a target gene into the vector, pDMSG1 is digested with Bsm I and the dsDNA oligonucleotides corresponding to either the sense or the antisense target RNA sequence, with Bsm I sticky ends, are ligated to the vector (see FIG. 5) to generate a single cassette-bearing plasmid (see, also, SEQ ID NO:45). A combination of two such plasmids, encoding the sense and antisense intermediate siRNA, can be co-transfected into cells to silence any target gene for which the siRNA is specific. A template sequence of a targeted gene (in sense orientation) can about 15 to 30 nucleotides (e.g., a 17 nucleotide) region that starts with AAG and ends with C, and generally is followed by about a 1 to 5 nucleotide overhang, for example, 1, 2, 3, 4 or 5 thymidine residues.

Other restriction sites can be used to make other vectors that have different sequence requirements. For example, the sequence between the last base of the promoter and the first base of the 5' terminator of plasmid pDMSGGFP(+) (Example 5) can be replaced with the nucleotide sequence, GAGACG-N25-CGTCTC (SEQ. ID. NO:27; only the sense strand is shown) to generate vector pDMSG2 (see FIG. 6; see, also, SEQ ID NO:46). When a template sequence against a target gene is to be inserted into the vector, DMSG2 is digested with BsmB I (or an isoschizomer such as EspI3, which has the same restriction endonuclease recognition site, ACCTGC(N)$_{4/8}$, SEQ ID NO:33) and a dsDNA oligonucleotide corresponding to either the sense or the antisense RNA, with BsmB I sticky ends, which do not support self-ligation, are ligated to the vector (FIG. 4) to generate a single-cassette-bearing plasmid (see, also, SEQ ID NO:47). By using two different insertion sites, both plus and minus cassettes can be carried on one vector.

Example 7

DMSG Cassettes Under the Control of T7 Promoter

A sufficient amount of siRNA can be produced inside cells using, for example, a DMSG cassette containing transcriptional regulatory elements that are specific for T7 RNA polymerase, which can be expressed from an encoding plasmid cotransfected with the DMSG cassette(s) into the cells, and that utilize a "run-off" mechanism.

DMSG cassettes containing a T7 RNA polymerase promoter can be prepared according to the methods described in Example 1, and using oligonucleotides as shown below, which include a template nucleotide sequence specific for GFP:

```
T7GFP(+)ROs:
5'-taatac gactcactat aGGAACG GCATC AAGGT GAAC TT-3'  (SEQ ID NO:28;
39 nucleotides);

T7GFP(+)ROa:
5'-AA GTTC ACCTT GATGC CGTTCCt atagtgagtc gtatta-3'  (SEQ ID NO:29; 39 nucleotides);

T7GFP(-)ROs:
5'-taatac gactcactat aGGTTCA CCTTG ATGCC GTTC TT-3'  (SEQ ID NO:30; 38 nucleotides);

T7GFP(-)ROa:
5'-AA GAAC GGCAT CAAGG TGAACCt atagtgagtc gtatta-3'  (SEQ ID NO:31;
38 nucleotides).
```

Alternatively, the transcription of siRNAs by T7 pol may be terminated by a single or multiple class II terminator (ATCTGTT, SEQ ID NO:32; (He et al., *J. Biol. Chem.* 30:18802-18811, 1998) in tandem. As the actual termination normally occurs 3 to 7 nucleotides downstream of this signal, this would leave a 3' portion not matching the sense or antisense sequence of the target mRNA. However, in case of siRNA produced via a hairpin intermediate, an overhang at the 3' end did not affect the RNAi effects (Paul et al., *Nat. Biotechnol.* 5:505-508, 2002). Transcription by phage RNA polymerases such as Sp6 and T7 pol also terminate at poly(T) containing arrest sites such as site Ia (GGGACGTTTTTTTCCC; SEQ ID NO:42) or related site II (TTTTTTC; SEQ ID NO:43; (Mote and Reines, *J. Biol. Chem.* 27:16843-16852, 1998), which conveniently can be used to produce siRNA or shRNA. Using a construct and methods as disclosed herein, expression of the T7 polymerase further can be controlled by expressing it, for example, from a tissue specific or developmental stage specific promoter such that RNAi mediated by the DMSG cassette can be achieved in a temporal, spatial, and cell type specific manner.

Although the invention has been described with reference to the above examples, it will be understood that modifications and variations are encompassed within the spirit and scope of the invention. Accordingly, the invention is limited only by the following claims.

What is claimed is:

1. A DNA-mediated silencing of gene (DMSG) cassette, comprising, in operative linkage, a distal sequence element (DSE), an RNA polymerase III (pol III) promoter, an expressible template nucleotide sequence, and at least one pol III terminator,
   wherein the terminator comprises SEQ ID NO:50,
   wherein the DSE is about −79 to −72 nucleotides upstream of the expressible template nucleotide sequence,
   wherein the expressible template nucleotide sequence is heterologous with respect to the pol III promoter,
   wherein the expressible template nucleotide sequence consists of at least about 16 nucleotides encoding an intermediate small interfering ribonucleic acid (RNA) molecule (siRNA), which mediates RNA interference of a target RNA, said intermediate siRNA comprising:
      a) a 5' portion, which comprises at least about 15 nucleotides complementary to a sense strand of the target RNA, and, optionally,
         a 3' terminal portion, comprising about 1 to 5 nucleotides,
         wherein the intermediate siRNA selectively hybridizes to the sense strand of the target RNA; or
      b) a 5' portion, which comprises at least about 15 nucleotides complementary to an antisense strand of the target RNA, and, optionally,
         a 3' terminal portion, comprising about 1 to 5 nucleotides,
         wherein the intermediate siRNA selectively hybridizes to the antisense strand of the target RNA, and wherein the encoded intermediate siRNA does not activate PKR in a mammalian cell.

2. The DMSG cassette of claim 1, wherein the intermediate siRNA is about 21 to 23 nucleotides in length.

3. The DMSG cassette of claim 1, wherein the 3' terminal portion of the intermediate siRNA is about 1 to 4 nucleotides in length.

4. The DMSG cassette of claim 1, wherein the pol III promoter or pol III terminator comprises a mammalian U6 gene pol III promoter or pol III terminator.

5. The DMSG cassette of claim 4, wherein the mammalian U6 gene is a human U6 gene or a mouse U6 gene.

6. The DMSG cassette of claim 1, further comprising an enhancer which is a constitutively active enhancer or an inducible enhancer.

7. The DMSG cassette of claim 1, which is a double stranded DNA molecule.

8. The DMSG cassette of claim 7, wherein one strand of the double stranded DNA molecule encodes a first intermediate siRNA, which is complementary to the sense strand of the target RNA,
   wherein a second strand of the double stranded DNA molecule encodes a second intermediate siRNA, which is complementary to the antisense strand of the target RNA, and
   wherein first intermediate siRNA and second siRNA selectively hybridize to form a double stranded siRNA.

9. The DMSG cassette of claim 8, wherein the double stranded siRNA comprises a 3' overhang of 1 to 4 nucleotides at each 3' terminus.

10. A vector, comprising the DMSG cassette of claim 1.

11. A isolated cell, which contains the DMSG cassette of claim 1.

12. The DMSG cassette of claim 1, wherein the expressible template nucleotide sequence encodes a first intermediate siRNA, and
   wherein the expressible template nucleotide sequence is operatively linked to a second expressible template nucleotide sequence encoding a second intermediate siRNA,
   wherein the 5' portion of the second intermediate siRNA is complementary to the 5' portion of the first intermediate siRNA, whereby, upon expression, the 5' portion of the first intermediate siRNA selectively hybridizes to the 5' portion of the second intermediate siRNA, thereby forming a hairpin structure.

13. The DMSG cassette of claim 1, comprising, in operative linkage,
   a) a sense polynucleotide sequence comprising nucleotides 6 to 13 of SEQ ID NO:1, nucleotide 19 to 38 of SEQ ID NO:1, nucleotides 66 to 69 of SEQ ID NO:1, the template nucleotide sequence, and at least one transcriptional terminator comprising a TTTT tetranucleotide sequence;
   b) an antisense polynucleotide complementary to any of the nucleotide sequences of a); or
   c) a double stranded polynucleotide comprising the sense polynucleotide of a) and the antisense polynucleotide of b).

14. The DMSG cassette of claim 1, further comprising a detectable label, a targeting moiety, or a combination thereof.

15. A plurality of DMSG cassettes, comprising at least two of the DMSG cassettes of claim 1.

16. The plurality of DMSG cassettes of claim 15, wherein the expressible template nucleotide sequence of a first DMSG cassette of the plurality encodes an intermediate siRNA comprising a 5' portion complementary to the sense strand of the target RNA of the target RNA.

17. The plurality of DMSG cassettes of claim 16, wherein the expressible template nucleotide sequence of at least a second DMSG cassette encodes an intermediate siRNA comprising a 5' portion complementary to the antisense strand of the target RNA.

\* \* \* \* \*

SEQUENCE LISTING

<160> NUMBER OF SEQ ID NOS: 51

<210> SEQ ID NO 1
<211> LENGTH: 113
<212> TYPE: DNA
<213> ORGANISM: Artificial sequence
<220> FEATURE:
<223> OTHER INFORMATION: Synthetic oligonucleotide

<400> SEQUENCE: 1

```
gatctatttg catggactat catatgctta ccgtaacttg aaagtatttc gatttcttgg      60
ctttatatat cttgtggaaa ggacgaaaca ccgaacggca tcaaggtgaa ctt           113
```

<210> SEQ ID NO 2
<211> LENGTH: 109
<212> TYPE: DNA
<213> ORGANISM: Artificial sequence
<220> FEATURE:
<223> OTHER INFORMATION: Synthetic oligonucleotide

<400> SEQUENCE: 2

```
aagttcacct tgatgccgtt cggtgtttcg tcctttccac aagatatata agccaagaa      60 atcgaaatac tttcaagtta cggtaagcat atgatagtcc atgcaaata              109
```

<210> SEQ ID NO 3
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 3

```
gatctatttg catggactat catatgctta ccgtaacttg aaagtatttc gatttcttgg      60
ctttatatat cttgtggaaa ggacgaaaca ccgaacggca tcaaggtgaa cttttacag     120 tttttg                                                              126
```

<210> SEQ ID NO 4
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 4

```
ctagcaaaaa ctgtaaaaag ttcaccttga tgccgttcgg tgtttcgtcc tttccacaag      60
atatataaag ccaagaaatc gaaatacttt caagttacgg taagcatatg atagtccatg     120
caaata                                                              126
```

<210> SEQ ID NO 5
<211> LENGTH: 113
<212> TYPE: DNA
<213> ORGANISM: Artificial sequence
<220> FEATURE:
<223> OTHER INFORMATION: Synthetic oligonucleotide

<400> SEQUENCE: 5

```
gatctatttg catggactat catatgctta ccgtaacttg aaagtatttc gatttcttgg      60
ctttatatat cttgtggaaa ggacgaaaca ccgttcacct tgatgccgtt ctt           113
```

<210> SEQ ID NO 6
<211> LENGTH: 109
<212> TYPE: DNA
<213> ORGANISM: Artificial sequence
<220> FEATURE:
<223> OTHER INFORMATION: Synthetic oligonucleotide

<400> SEQUENCE: 6

```
aagaacggca tcaaggtgaa cggtgtttcg tcctttccac aagatatata aagccaagaa    60
atcgaaatac tttcaagtta cggtaagcat atgatagtcc atgcaaata              109
```

<210> SEQ ID NO 7
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 7

```
gatctatttg catggactat catatgctta ccgtaacttg aaagtatttc gatttcttgg    60
ctttatatat cttgtggaaa ggacgaaaca ccgttcacct tgatgccgtt cttttttacag  120
tttttg                                                              126
```

<210> SEQ ID NO 8
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 8

```
ctagcaaaaa ctgtaaaaag aacggcatca aggtgaacgg tgtttcgtcc tttccacaag    60
atatataaag ccagaaaatc gaaatacttt caagttacgg taagcatatg atagtccatg   120
caaata                                                              126
```

<210> SEQ ID NO 9
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 9

```
ctagcaaaaa ctgtaaaaag aacggcatga aggtgaacgg tgtttcgtcc tttccacaag    60
atatataaag ccagaaaatc gaaatacttt caagttacgg taagcatatg atagtccatg   120
caaata                                                              126
```

<210> SEQ ID NO 10
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 10

```
ctagcaaaaa ctgtaaaaag aacgggatga aggtgaacgg tgtttcgtcc tttccacaag    60
atatataaag ccagaaaatc gaaatacttt caagttacgg taagcatatg atagtccatg   120
caaata                                                              126
```

<210> SEQ ID NO 11

```
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 11
ctagcaaaaa ctgtaaatag aacggcatca aggtgaaggg tgtttcgtcc tttccacaag      60
atatataaag ccaagaaatc gaaatacttt caagttacgg taagcatatg atagtccatg     120
caaata                                                                126

<210> SEQ ID NO 12
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 12
ctagcaaaaa ctgtaaaaag aacggcatca aggtgatggg tgtttcgtcc tttccacaag      60
atatataaag ccaagaaatc gaaatacttt caagttacgg taagcatatg atagtccatg     120
caaata                                                                126

<210> SEQ ID NO 13
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 13
gatctatttg catggactat catatgctta ccgtaacttg aa                         42

<210> SEQ ID NO 14
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 14
agtatttcga tttcttggct ttatatatct tgtggaaagg acga                       44

<210> SEQ ID NO 15
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 15
aacaccgttc accttgatgc cgttcttttt acagttttg                             40

<210> SEQ ID NO 16
<211> LENGTH: 66
<212> TYPE: DNA
<213> ORGANISM: Artificial sequence
<220> FEATURE:
<223> OTHER INFORMATION: Synthetic oligonucleotide

<400> SEQUENCE: 16
ctagcaaaaa ctgtaaaaag aacggcatca aggtgaacgg tgtttcgtcc tttccacaag      60
atatat                                                                66
```

```
<210> SEQ ID NO 17
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 17
aaagccaaga aatcgaaata ctttcaagtt acggtaagca tatgatagtc catgcaaata        60

<210> SEQ ID NO 18
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 18
gatctatttg catacaaaag gaaactcacc ctaactgtaa agtaattgtg tgttttgaga        60
ctataaatat cccttggaga aaagccttgt ttggtaaaca gttgattgaa cttttgttcg       120
tttttg                                                                126

<210> SEQ ID NO 19
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 19
gatctatttg catacaaaag gaaactcacc ctaactgtaa agtaattgtg tgttttgaga        60
ctataaatat cccttggaga aaagccttgt ttgttcaatc aactgtttac cttttgttcg       120
tttttg                                                                126

<210> SEQ ID NO 20
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 20
ctagcaaaaa cgaacaaaag ttcaatcaac tgtttaccaa acaaggcttt tctccaaggg        60
atatttatag tctcaaaaca cacaattact ttacagttag ggtgagtttc cttttgtatg       120
caaata                                                                126

<210> SEQ ID NO 21
<211> LENGTH: 126
<212> TYPE: DNA
<213> ORGANISM: Artificial sequence
<220> FEATURE:
<223> OTHER INFORMATION: Synthetic oligonucleotide

<400> SEQUENCE: 21
ctagcaaaaa cgaacaaaag gtaaacagtt gattgaacaa acaaggcttt tctccaaggg        60
atatttatag tctcaaaaca cacaattact ttacagttag ggtgagtttc cttttgtatg       120
caaata                                                                126

<210> SEQ ID NO 22
```

```
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 22
gattatttgc atacaaaagg aaactcaccc taactgtaaa gtaattgtgt gttttgagac    60
ta                                                                 62

<210> SEQ ID NO 23
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 23
taaatatccc ttggagaaaa gccttgtttg ttcaatcaac tgtttacctt ttgttcgttt    60
ttt                                                                63

<210> SEQ ID NO 24
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 24
ctagcaaaaa cgaacaaaag gtaaacagtt gattgaacaa acaaggcttt tctccaaggg    60
at                                                                 62

<210> SEQ ID NO 25
<211> LENGTH: 62
<212> TYPE: DNA
<213> ORGANISM: Artificial sequence
<220> FEATURE:
<223> OTHER INFORMATION: Synthetic oligonucleotide

<400> SEQUENCE: 25
tttatagtct caaaacacac aattacttta cagttagggt gagtttcctt ttgtatgcaa    60
at                                                                 62

<210> SEQ ID NO 26
<211> LENGTH: 36
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(36)
<223> OTHER INFORMATION: n is any nucleotide

<400> SEQUENCE: 26
cattcnnnnn nnnnnnnnnn nnnnnnnnnn gaatgc                            36

<210> SEQ ID NO 27
<211> LENGTH: 37
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (1)..(37)
<223> OTHER INFORMATION: n is any nucleotide

<400> SEQUENCE: 27
gagacgnnnn nnnnnnnnnn nnnnnnnnnn ncgtctc                                37

<210> SEQ ID NO 28
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 28
taatacgact cactatagga acggcatcaa ggtgaactt                               39

<210> SEQ ID NO 29
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 29
aagttcacct tgatgccgtt cctatagtga gtcgtatta                               39

<210> SEQ ID NO 30
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 30
taatacgact cactataggt tcaccttgat gccgttctt                               39

<210> SEQ ID NO 31
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 31
aagaacggca tcaaggtgaa cctatagtga gtcgtatta                               39

<210> SEQ ID NO 32
<211> LENGTH: 7
<212> TYPE: DNA
<213> ORGANISM: Artificial sequence
<220> FEATURE:
<223> OTHER INFORMATION: Synthetic oligonucleotide

<400> SEQUENCE: 32 atctgtt                                                                  7

<210> SEQ ID NO 33
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(14)
<223> OTHER INFORMATION: n is any nucleotide
<220> FEATURE:
```

```
<221> NAME/KEY: misc_feature
<222> LOCATION: (11)..(14)
<223> OTHER INFORMATION: nt. 11 - 14 are optionally present

<400> SEQUENCE: 33
acctgcnnnn nnnn                                                      14

<210> SEQ ID NO 34
<211> LENGTH: 20
<212> TYPE: DNA
<213> ORGANISM: Homo sapiens

<400> SEQUENCE: 34
cttaccgtaa cttgaaagta                                                20

<210> SEQ ID NO 35
<211> LENGTH: 20
<212> TYPE: DNA
<213> ORGANISM: Murine

<400> SEQUENCE: 35
ctcaccctaa ctgtaaagta                                                20

<210> SEQ ID NO 36
<211> LENGTH: 265
<212> TYPE: DNA
<213> ORGANISM: Homo sapiens

<400> SEQUENCE: 36
aaggtcgggc aggaagaggg cctatttccc atgattcctt catatttgca tatacgatac    60
aaggctgtta gagagataat tagaattaat ttgactgtaa acacaaagat attagtacaa   120
aatacgtgac gtagaaagta ataatttctt gggtagtttg cagttttaa aattatgttt    180 taaaatggac tatcatatgc ttaccgtaac ttgaaagtat ttcgatttct tggctttata   240
tatcttgtgg aaaggacgaa acacc                                         265

<210> SEQ ID NO 37
<211> LENGTH: 16
<212> TYPE: DNA
<213> ORGANISM: T7 bacteriophage

<400> SEQUENCE: 37
taatacgact cactat                                                    16

<210> SEQ ID NO 38
<211> LENGTH: 87
<212> TYPE: DNA
<213> ORGANISM: Artificial sequence
<220> FEATURE:
<223> OTHER INFORMATION: modified U6 gene enhancer
<220> FEATURE:
<221> NAME/KEY: misc_feature
<222> LOCATION: (8)..(67)
<223> OTHER INFORMATION: n is any nucleotide
<220> FEATURE:
<221> NAME/KEY: misc_feature
<222> LOCATION: (18)..(67)
<223> OTHER INFORMATION: nt. 18 - 67 are optionally present

<400> SEQUENCE: 38
attgcatnnn nnnnnnnnn nnnnnnnnn nnnnnnnnn nnnnnnnnn nnnnnnnnn         60 nnnnnnnctt accgtaactt gaaagta                                        87
```

```
<210> SEQ ID NO 39
<211> LENGTH: 87
<212> TYPE: DNA
<213> ORGANISM: Artificial sequence
<220> FEATURE:
<223> OTHER INFORMATION: modified U6 gene enhancer
<220> FEATURE:
<221> NAME/KEY: misc_feature
<222> LOCATION: (8)..(67)
<223> OTHER INFORMATION: n is any nucleotide
<220> FEATURE:
<221> NAME/KEY: misc_feature
<222> LOCATION: (18)..(67)
<223> OTHER INFORMATION: nt. 18 - 67 are optionally present

<400> SEQUENCE: 39
attgcatnnn nnnnnnnnnn nnnnnnnnnn nnnnnnnnnn nnnnnnnnnn nnnnnnnnnn      60
nnnnnnnctc accctaactg taaagta                                          87

<210> SEQ ID NO 40
<211> LENGTH: 40
<212> TYPE: DNA
<213> ORGANISM: Artificial sequence
<220> FEATURE:
<223> OTHER INFORMATION: modified U6 gene enhancer
<220> FEATURE:
<221> NAME/KEY: misc_feature
<222> LOCATION: (1)..(40)
<223> OTHER INFORMATION: n is any nucleotide

<400> SEQUENCE: 40
attgcatnnn nnnnnnnnnn cttaccgtaa cttgaaagta                            40

<210> SEQ ID NO 41
<211> LENGTH: 40
<212> TYPE: DNA
<213> ORGANISM: Artificial sequence
<220> FEATURE:
<223> OTHER INFORMATION: modified U6 gene enhancer
<220> FEATURE:
<221> NAME/KEY: misc_feature
<222> LOCATION: (1)..(40)
<223> OTHER INFORMATION: n is any nucleotide

<400> SEQUENCE: 41
attgcatnnn nnnnnnnnnn ctcaccctaa ctgtaaagta                            40

<210> SEQ ID NO 42
<211> LENGTH: 16
<212> TYPE: DNA
<213> ORGANISM: SP6 bacteriophage

<400> SEQUENCE: 42
gggacgtttt tttccc                                                     16

<210> SEQ ID NO 43
<211> LENGTH: 7
<212> TYPE: DNA
<213> ORGANISM: SP6 bacteriophage

<400> SEQUENCE: 43 tttttc                                                                7

<210> SEQ ID NO 44
<211> LENGTH: 43
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<222> LOCATION: (1)..(43)
<223> OTHER INFORMATION: n is any nucleotide

<400> SEQUENCE: 44
accgcattcn nnnnnnnnn nnnnnnnnnn nnnngaatgc ttt                43

<210> SEQ ID NO 45
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(20)
<223> OTHER INFORMATION: n is any nucleotide
<220> FEATURE:
<221> NAME/KEY: misc_feature
<222> LOCATION: (19)..(20)
<223> OTHER INFORMATION: nt. 19 - 20 are optionally present

<400> SEQUENCE: 45
accgnnnnnn nnnnnnnnnn cttt                                    24

<210> SEQ ID NO 46
<211> LENGTH: 47
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(47)
<223> OTHER INFORMATION: n is any nucleotide

<400> SEQUENCE: 46
acaccgagac gnnnnnnnnn nnnnnnnnnn nnnnncgtc tctttt              47

<210> SEQ ID NO 47
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(22)
<223> OTHER INFORMATION: n is any nucleotide
<220> FEATURE:
<221> NAME/KEY: misc_feature
<222> LOCATION: (21)..(22)
<223> OTHER INFORMATION: nt. 21 - 22 are optionally present

<400> SEQUENCE: 47
acaccgnnnn nnnnnnnnnn nnctttt                                 28

<210> SEQ ID NO 48
<211> LENGTH: 11
<212> TYPE: DNA
<213> ORGANISM: Homo sapiens

<400> SEQUENCE: 48
tttttacatc a                                                  11

<210> SEQ ID NO 49
<211> LENGTH: 9

```
<212> TYPE: DNA
<213> ORGANISM: Mouse

<400> SEQUENCE: 49 ttttgttcc                                                                        9

<210> SEQ ID NO 50
<211> LENGTH: 15
<212> TYPE: DNA
<213> ORGANISM: Artificial sequence
<220> FEATURE:
<223> OTHER INFORMATION: Modified human RNA polymerase III terminator

<400> SEQUENCE: 50
tttttacagt ttttg                                                                15

<210> SEQ ID NO 51
<211> LENGTH: 15
<212> TYPE: DNA
<213> ORGANISM: Artificial sequence
<220> FEATURE:
<223> OTHER INFORMATION: Modified mouse RNA polymerase III terminator

<400> SEQUENCE: 51
ttttgttcgt ttttg                                                                15
```